(12) United States Patent
Honda

(10) Patent No.: US 8,531,513 B2
(45) Date of Patent: Sep. 10, 2013

(54) ASSEMBLY METHOD FOR ENDOSCOPE IMAGE PICKUP UNIT AND ENDOSCOPE

(75) Inventor: Kazuki Honda, Higashiyamato (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/616,191

(22) Filed: Sep. 14, 2012

(65) Prior Publication Data

US 2013/0070072 A1 Mar. 21, 2013

Related U.S. Application Data

(63) Continuation of application No. PCT/JP2012/053537, filed on Feb. 15, 2012.

(30) Foreign Application Priority Data

Mar. 31, 2011 (JP) ................................. 2011-080252

(51) Int. Cl.
*A62B 1/04* (2006.01)
*A61B 1/04* (2006.01)
*H04N 7/18* (2006.01)
*H04N 9/47* (2006.01)

(52) U.S. Cl.
USPC .............................................. 348/76; 348/65

(58) Field of Classification Search
USPC ....................................................... 348/65, 76
See application file for complete search history.

(56) References Cited

U.S. PATENT DOCUMENTS

| | | |
|---|---|---|
| 2004/0254424 A1 | 12/2004 | Simkulet et al. |
| 2008/0045797 A1 | 2/2008 | Yasushi et al. |
| 2008/0221388 A1 | 9/2008 | Seibel et al. |
| 2010/0091385 A1 | 4/2010 | Togino |
| 2010/0312057 A1 | 12/2010 | Konno |

FOREIGN PATENT DOCUMENTS

| | | |
|---|---|---|
| EP | 1 769 718 A1 | 4/2007 |
| EP | 2 385 406 A1 | 11/2011 |
| JP | 05-269081 A | 10/1993 |
| JP | 10-174675 A | 6/1998 |
| JP | 2008-309861 A | 12/2008 |
| WO | WO 2006/004083 A1 | 1/2006 |
| WO | WO 2008/153114 A1 | 12/2008 |
| WO | 2010/084914 A1 | 7/2010 |

OTHER PUBLICATIONS

European Search Report dated Mar. 28, 2013 from corresponding European Application No. 12 76 3127.3.

*Primary Examiner* — Allen Wong
(74) *Attorney, Agent, or Firm* — Scully, Scott, Murphy & Presser, P.C.

(57) ABSTRACT

In an assembly method for an endoscope image pickup unit, the endoscope image pickup unit includes a distal end portion main body portion including a front opening portion, a side opening portion, a rear opening portion and an arrangement space portion, a lens section including a distal end lens having an outer diameter that generally fits in the front opening portion, and an image pickup section that fits in the rear opening portion and includes an image pickup device arranged in an image forming position by a lens system such as the lens section. The assembly method includes steps for inserting the lens section into the arrangement space portion from the side opening portion, fitting the inserted lens section in the front opening portion, and fitting the image pickup section in the rear opening portion from a rear of the rear opening portion.

13 Claims, 18 Drawing Sheets

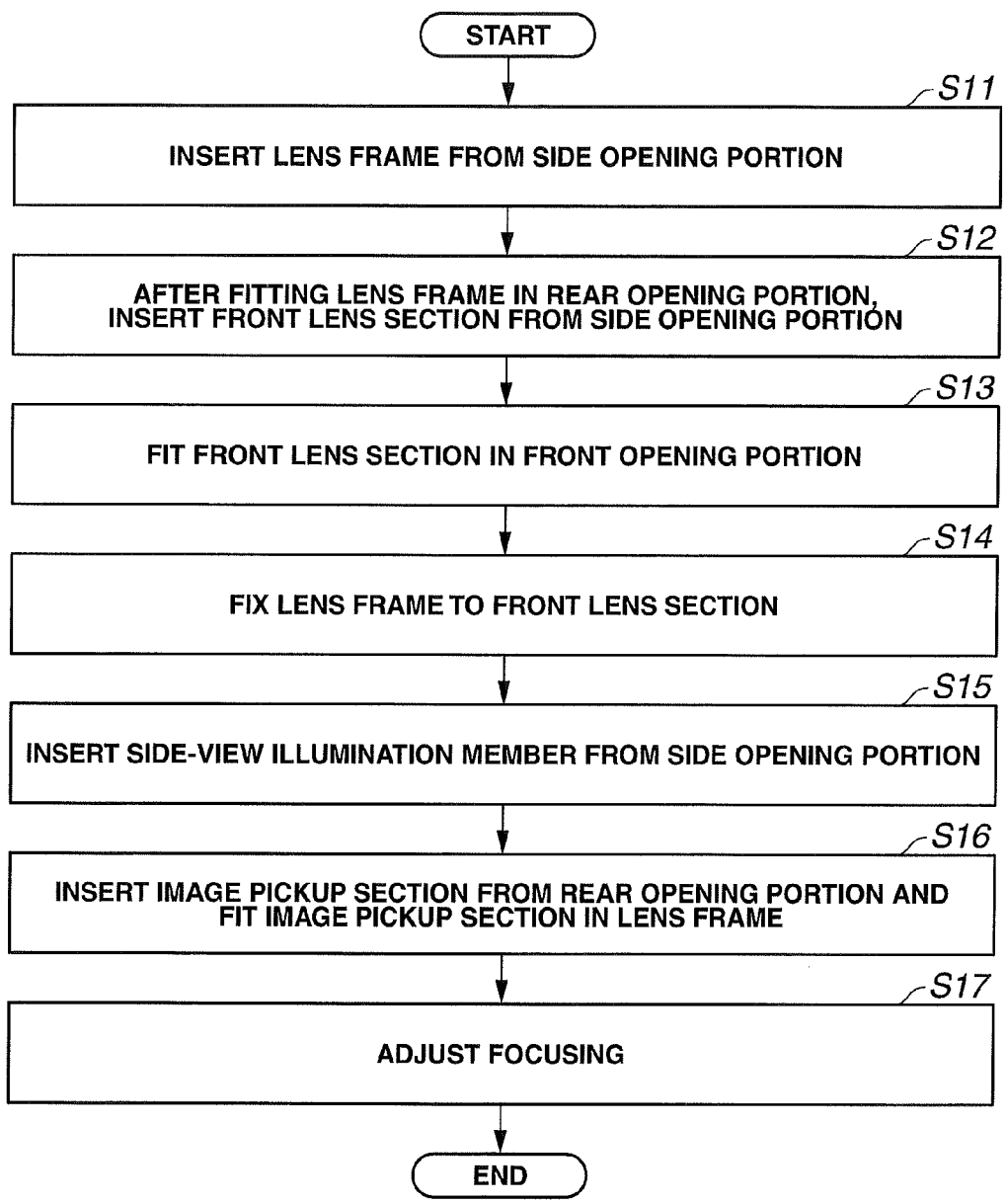

US 8,531,513 B2

ASSEMBLY METHOD FOR ENDOSCOPE IMAGE PICKUP UNIT AND ENDOSCOPE

CROSS REFERENCE TO RELATED APPLICATION

This application is a continuation application of PCT/JP2012/053537 filed on Feb. 15, 2012 and claims benefit of Japanese Application No. 2011-080252 filed in Japan on Mar. 31, 2011, the entire contents of which are incorporated herein by this reference.

BACKGROUND OF THE INVENTION

1. Field of the Invention

The present invention relates to an assembly method for an endoscope image pickup unit incorporating an image pickup unit at a distal end portion of an insertion portion and an endoscope.

2. Description of the Related Art

In recent years, an endoscope in which an image pickup unit is provided at a distal end portion of an insertion portion has been widely used in a medical field such as an examination of an inside of a body cavity.

When the insertion portion is inserted into the body cavity or the like, it is possible to secure satisfactory insertion properties by reducing a size of the image pickup unit provided at the distal end portion of the insertion portion. Therefore, various assembly methods for the image pickup unit incorporated in the distal end portion of the insertion portion have been proposed.

For example, a related art of Japanese Patent Application Laid-Open Publication No. 05-269081 discloses an assembly method for an endoscope image pickup unit in which an image pickup unit is incorporated at a distal end portion of an insertion portion.

In the related art, an objective lens system and an image pickup device are assembled together to assemble an image pickup unit. The assembled image pickup unit is inserted from a rear opening portion provided at the distal end portion. The image pickup unit is fixed on an inside of the rear opening portion to thereby be assembled as an endoscope image pickup unit.

In this case, the rear opening portion is set to a size for enabling the image pickup unit to pass from a rear side.

SUMMARY OF THE INVENTION

An assembly method for an endoscope image pickup unit according to an aspect of the present invention is an assembly method for an endoscope image pickup unit including: a distal end portion main body portion including a front opening portion, a side opening portion, and a rear opening portion functioning as opening portions respectively opened to a front, a side, and a rear and an arrangement space portion that communicates with the three opening portions; a lens section including a distal end lens having an outer diameter that generally fits in the front opening portion; and an image pickup section that fits in the rear opening portion and includes an image pickup device arranged in an image forming position by the lens section or an image pickup device arranged in an image forming position by the lens section and a rear lens section arranged to be integrated with the image pickup device in a rear of the lens section, the assembly method including: an inserting step for inserting the lens section into the arrangement space portion from the side opening portion; a fitting step for fitting the lens section, which is inserted into the arrangement space portion, in the front opening portion that communicates with the arrangement space portion; and an image pickup section fitting step for fitting the image pickup section in the rear opening portion from a rear of the rear opening portion.

An endoscope according to an aspect of the present invention includes an image pickup unit including: a distal end portion main body portion including a front opening portion, a side opening portion, and a rear opening portion functioning as opening portions respectively opened to a front, a side, and a rear and an arrangement space portion that communicates with the three opening portions; a lens section including a distal end lens having an outer diameter that generally fits in the front opening portion; and an image pickup section that fits in the rear opening portion and includes an image pickup device arranged in an image forming position by the lens section or an image pickup device arranged in an image forming position by the lens section and a rear lens section arranged to be integrated with the image pickup device in a rear of the lens section. The side opening portion is opened having an area equal to or larger than an area of projection to a side of the lens section to enable the lens section to be inserted from the side and opened having an area smaller than an area of projection to the side of the lens section and the image pickup section after assembly, and the rear opening portion is opened having an inner diameter smaller than a maximum outer diameter of the lens section and substantially the same as an outer diameter of the image pickup section.

BRIEF DESCRIPTION OF THE DRAWINGS

FIG. 8 is a flowchart showing an assembly method for an image pickup unit according to a second embodiment of the present invention;

DETAILED DESCRIPTION OF THE PREFERRED EMBODIMENTS

Embodiments of the present invention are explained below with reference to the drawings.
(First Embodiment)

Figure 1:
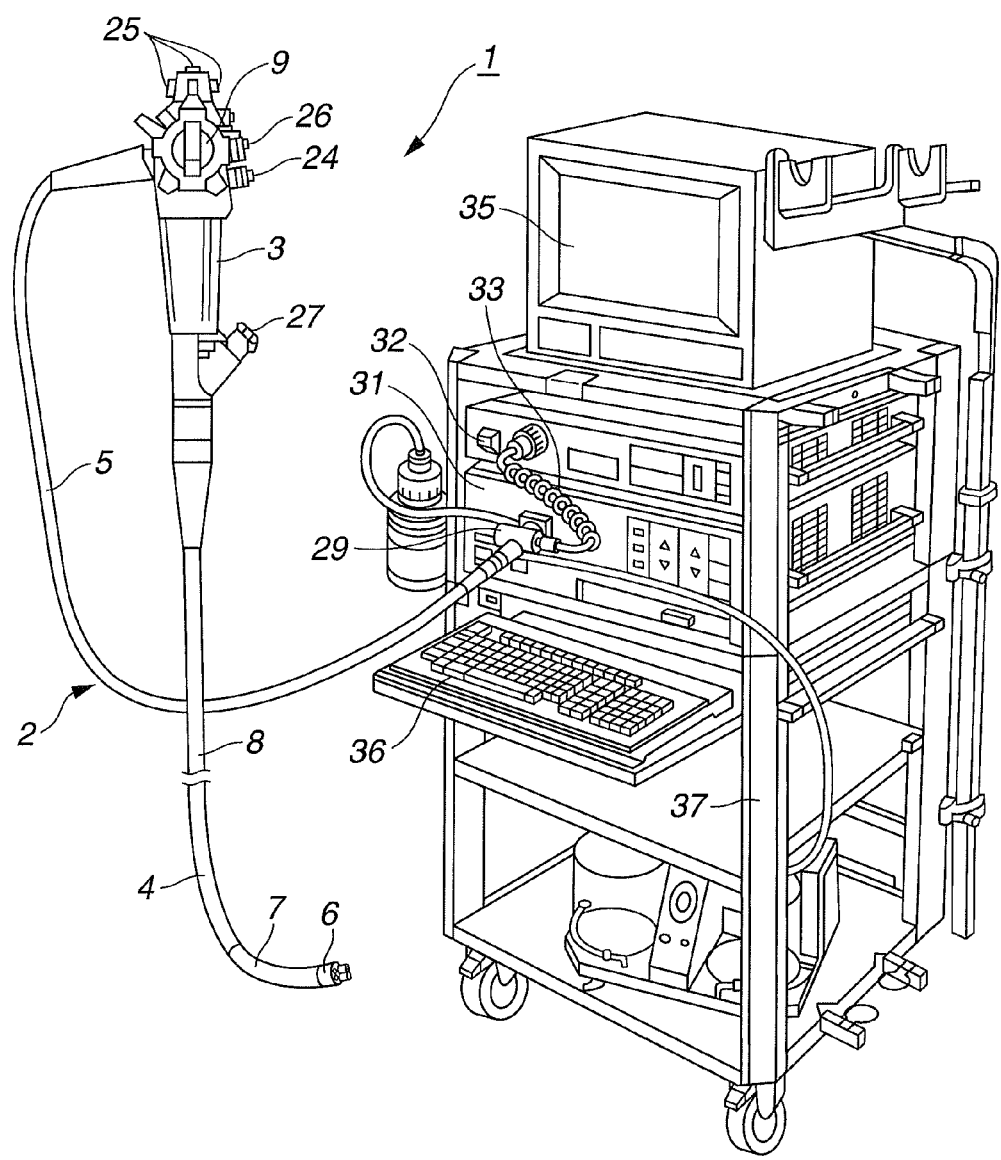
FIG. 1 is a perspective view showing an endoscope apparatus according to a first embodiment of the present invention.

As shown in FIG. 1, an endoscope apparatus 1 according to a first embodiment of the present invention includes an endoscope 2 for performing an endoscopic examination. The endoscope 2 is configured by an operation section 3 that a surgeon grips to perform operation, an elongated insertion portion 4 formed at a front end of the operation section 3 and inserted into a body cavity or the like, and a universal cord 5, a proximal end of which is extended from a side portion of the operation section 3.

The insertion portion 4 includes a rigid distal end portion 6 provided at a distal end of the insertion portion 4, a bendable bending portion 7 provided at a rear end of the distal end portion 6, and a long flexible tube portion 8 provided at a rear end of the bending portion 7 and having flexibility. Bending operation of the bending portion 7 can be performed by a bending operation lever 9 provided at the operation section 3.

Figure 2:
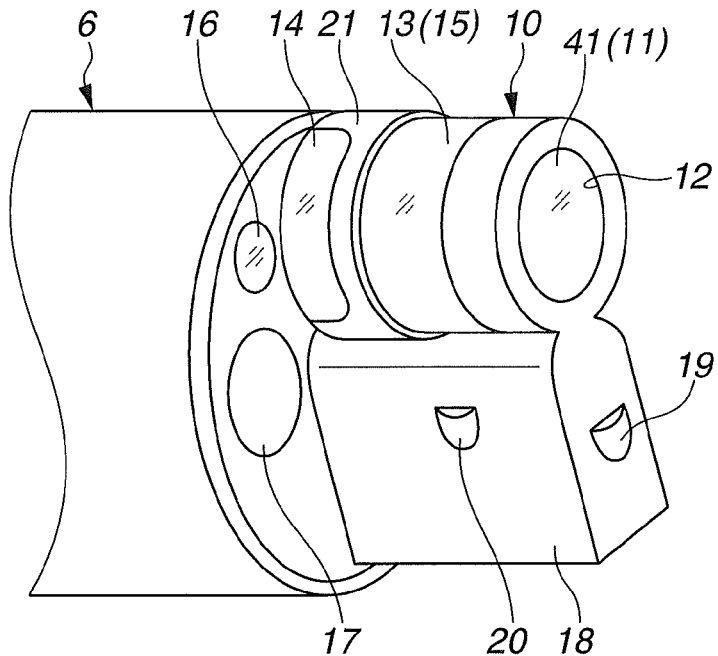
FIG. 2 is a perspective view showing a configuration of a distal end portion of an insertion portion of an endoscope.

As shown in FIG. 2, a cylindrical distal end portion 10 projecting in a cylindrical shape from a position eccentric to a vicinity above a center of a distal end face of the distal end portion 6 is formed at the distal end portion 6 of the insertion portion 4.

Figure 3:
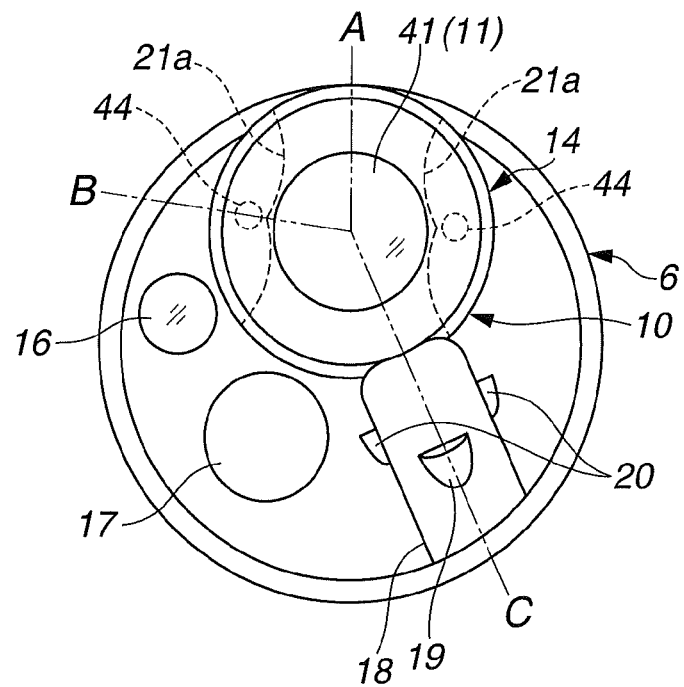
FIG. 3 is a front view showing the configuration of the distal end portion of the insertion portion.

An objective lens system 11 (see FIG. 4A) for both of a front view and a side view for performing an optical observation is attached on a distal end side of the cylindrical distal end portion 10. A front-view observation window 12 and a side-view observation window 13 functioning as windows for observation by the objective lens system 11 are formed. A side-view illumination window 14 (specifically, two side-view illumination windows 14 as shown in FIG. 3) for performing side-view illumination is formed in a vicinity of a proximal end of the cylindrical distal end portion 10. The side-view illumination window 14 is formed by a side-view illumination member 21 having an annular shape.

The side-view observation window 13 is formed in an annular shape to set an observation visual field near an entire circumference (excluding a lower end side) along a circumferential direction of a side surface of a cylindrical shape to observe a direction of the side surface. The side-view observation window 13 includes mirror lenses 15 functioning as objective lenses for side view including reflection surfaces for capturing light from an object, which is made incident from an arbitrary direction opposed to the annular shape, in an observation visual field (simply referred to as visual field as well) of the side view and acquiring the light as a side-view visual field image.

Note that, as explained below, a distal end lens 41 functioning as an objective lens for front view for acquiring an object image on a front side of the front-view observation window 12 is attached to the front-view observation window 12.

On the distal end face of the distal end portion 6 around the cylindrical distal end portion 10, a front-view illumination window 16 and a channel distal end opening portion 17 are provided. The front-view illumination window 16 is adjacent to the cylindrical distal end portion 10 to emit illumination light to an observation target side of the front-view visual field of the front-view observation window 12. The channel distal end opening portion 17 functions as an opening for projecting a treatment instrument inserted through into a channel.

In the present embodiment, a cylindrical distal end portion supporting member (hereinafter, supporting member) 18 is provided to project from the distal end face of the distal end portion 6. The cylindrical distal end portion supporting member 18 is adjacent to a lower portion side of the cylindrical distal end portion 10 to support the cylindrical distal end portion 10. The supporting member 18 supplements strength of the cylindrical distal end portion 10. The supporting member 18 is formed of a light blocking member having a function of optically blocking light.

Note that, in the present embodiment, the cylindrical distal end portion 10 and the supporting member 18 are formed of a same member. Proximal ends of the cylindrical distal end portion 10 and the supporting member 18 are integrally provided on the distal end face of the distal end portion 6 to form a distal end portion main body portion (hereinafter, main body portion) 61. However, structure may be adopted in which the cylindrical distal end portion 10 and the supporting member 18 are fixed to the distal end portion 6 by joining or the like.

In the supporting member 18, a nozzle portion for front-view observation window 19 and nozzle portions for side-view observation window 20 for respectively cleaning the front-view observation window 12 and the side-view observation window 13 of the objective lens system 11 are provided.

More specifically, the nozzle portion for front-view observation window 19 opened toward the front-view observation window 12 is provided on a distal end face of the supporting member 18.

The nozzle portions for side-view observation window 20 opened toward the side-view observation window 13 are provided on side surfaces of the supporting member 18. The supporting member 18 shields the nozzle portion for front-view observation window 19 and the nozzle portions for side-view observation window 20 not to appear in a side-view visual field image. As shown in FIG. 3, the nozzle portions for side-view observation window 20 are provided in two places.

In the operation section 3 shown in FIG. 1, an air and liquid supply operation button 24 is provided to enable air and liquid for cleaning to be respectively ejected from the nozzle portion for front-view observation window 19 and the nozzle portions for side-view observation window 20. Air supply and liquid supply can be switched by operation of the air and liquid supply operation button 24.

Note that, in an example shown in FIG. 1, one air and liquid supply operation button 24 is provided. However, two air and liquid supply operation buttons 24 may be provided.

In the operation section 3, a suction operation button 26 for sucking and collecting mucus and the like in a body cavity from the channel distal end opening portion 17 is disposed. A channel is formed by a not-shown tube or the like disposed in the insertion portion 4. The channel communicates with a treatment instrument insertion port 27 provided in a vicinity of a front end of the operation section 3.

When the surgeon intends to perform treatment by a treatment instrument, the surgeon can perform medical treatment by the treatment instrument by inserting the treatment instrument from the treatment instrument insertion port 27 and projecting a distal end side of the treatment instrument from the channel distal end opening portion 17.

A connector 29 is provided at an end of the universal cord 5. The connector 29 is connected to a light source device 31 of the endoscope. A pipe sleeve (not shown) to be a connection end portion of a fluid conduit projecting from a distal end of the connector 29 and a light guide pipe sleeve (not shown) to be a supply end portion of illumination light are detachably connected to the light source device 31. One end of a connection cable 33 is connected to an electric contact portion provided on a side surface of the light source device 31.

A connector at the other end of the connection cable 33 is electrically connected to a video processor 32 functioning as a signal processing device that performs signal processing for an image pickup device 34 (see FIG. 4A) that forms an endoscope image pickup unit (hereinafter simply referred to as image pickup unit) 60 mounted on the endoscope 2.

The video processor 32 supplies a driving signal for driving the image pickup device 34 (see FIG. 4A) mounted at the distal end portion 6 of the endoscope 2, applies signal processing to an image pickup signal (an image signal) outputted from the image pickup device 34 by the supply of the driving signal, and generates a video signal.

The video signal generated by the video processor 32 is outputted to a monitor 35 functioning as a display device. An image picked up by the image pickup device 34 is displayed on a display surface of the monitor 35 as an endoscope image. Peripheral devices such as the light source device 31, the video processor 32, and the monitor 35 are arranged on a stand 37 together with a keyboard 36 for performing input of patient information and the like.

Illumination light generated by the light source device 31 is guided (transmitted) to distal end face sides of a light guide, which is inserted through the operation section 3 and the insertion portion 4 from the universal cord 5, by the light guide. Distal end faces of the light guide inserted through the insertion portion 4 are arranged on an inner side of the side-view illumination window 14 and an inner side of the front-view illumination window 16 of the cylindrical distal end portion 10. Each of the distal end faces emits the guided light.

A distal end side of the light guide branches, for example, in the insertion portion 4. One distal end functions as a light guide 44 on an inside of the side-view illumination window 14 and the other functions as a not-shown light guide in the front-view illumination window 16.

The illumination light is expanded and emitted from the side-view illumination window 14 and the front-view illumination window 16 respectively to a distal end side in a side surface direction, which is a side-view visual field side, and a distal end side in an insertion direction (also referred to as longitudinal direction) of the insertion portion 4, which is a front-view visual field side.

Note that the front-view illumination window 16 emits the illumination light, which is emitted from the distal end face (an emission end face) of the light guide, to a front side via an illumination lens. On the other hand, the side-view illumination window 14 is formed to reflect the illumination light, which is emitted from the distal end face (an emission end face) of the light guide 44 to change a route to a substantially perpendicular direction and emit the illumination light to a side of the distal end portion 6.

Figure 4A:
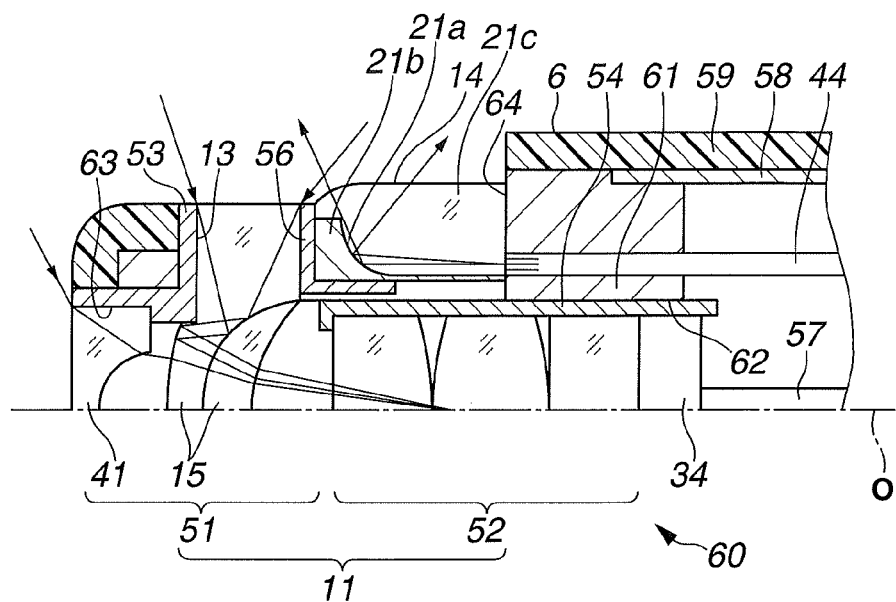
FIG. 4A is a sectional view showing structure around an objective lens system taken along an O-B cross section of FIG. 3.

FIG. 4A shows, using an O-B cross section of FIG. 3, a configuration of a peripheral portion of the objective lens system 11 for both of the front view and the side view and the side-view illumination window 14, which configure the image pickup unit 60.

In the main body portion 61, an arrangement space portion 65 (omitted in FIG. 4A, see FIG. 6A and the like) communicating with a front opening portion 63, a side opening portion 64, and a rear opening portion 62 explained below is formed. The objective lens system 11, which configures the image pickup unit 60, and an image pickup section 55 are incorporated in the arrangement space portion 65.

On an optical axis O coinciding with an image pickup center extending along a center axis of the cylindrical distal end portion 10 projecting from the distal end portion 6, a front lens section 51 including a distal end lens 41 and the mirror lenses 15 each formed in a rotationally symmetrical shape and a rear lens section 52 including a plurality of lenses are arranged to form the objective lens system 11 that forms an image on an image pickup surface of the image pickup device 34. A cover glass is provided on a front surface of the image pickup device 34.

In the present embodiment, the distal end lens 41 and the mirror lenses 15 are fixed to and integrated with a lens frame 53.

The rear lens section 52 is fixed to a lens frame (an image pickup frame) 54 together with the image pickup device 34 to form the image pickup section 55. A signal cable 57 is connected to a rear surface of the image pickup device 34. A distal end of a pipe 58 connected to a bending piece of the bending portion 7 (see FIG. 1) is firmly fixed to an outer circumferential surface close to a rear end of the main body portion 61. An outer circumferential side of the pipe 58 is covered with a distal end cover 59.

Note that, in an assembly method according to the present embodiment, the front lens section 51 is configured to be integrated with a lens frame 56 (in a second embodiment explained below, the front lens section 51 is assembled to be separated from the lens frame 56).

At the rear end of the main body portion 61, the rear opening portion 62 set to an opening inner diameter (hereinafter simply referred to as inner diameter as well) for enabling the lens frame 54 of the image pickup section 55 to pass is provided. The distal end lens 41, which configures the objective lens system 11, forms, via the circular front-view observation window 12, a wide-angle front-view visual field having an observation visual field on a distal end side of the distal end lens 41 extending along the insertion direction of the insertion portion 4.

Note that the front opening portion 63, which forms the front-view observation window 12 on a front surface of the cylindrical distal end portion 10, is set to an opening inner diameter for enabling the lens frame 53, to which the distal end lens 41 is attached, to be fitted and attached. Therefore, the distal end lens 41 generally fits in the opening inner diameter of the front opening portion 63.

The mirror lenses 15 functioning as objective lenses for side view for forming an object image on a side making use of a reflection surface, which is arranged immediately behind the distal end lens 41, and refraction are configured by joining two lenses that reflect light, which made incident from a side surface direction, twice on a joining surface and a front surface as shown in FIG. 4A and then refract and guide the light to the rear lens section 52 side. In the figures other than FIG. 4A, the mirror lenses 15 are simplified and shown as one mirror lens 15.

With the mirror lenses 15, outer circumferential surfaces of which are exposed to the side-view observation window 13, the side-view observation window 13 has a substantially annular side-view observation visual field that covers nearly an entire circumference in a circumferential direction of the insertion portion while having, centering around a direction orthogonal to an insertion portion long axis direction, a side-view visual field for enabling an appropriate angle range to be observed from the orthogonal direction.

Note that FIG. 4A shows schematic paths of a beam made incident on the distal end lens 41, which forms the front-view observation window 12, from an object side in a visual field of the distal end lens 41 and a beam made incident on the mirror lenses 15, which form the side-view observation window 13, from an object side in a side-view visual field of the mirror lenses 15.

On the image pickup surface of the image pickup device 34, an object image in a front-view visual field from an insertion direction on a front side of the distal end lens 41 of the front-view observation window 12 is formed in a circular shape on a center side of the image pickup surface. The object image is acquired as a front-view visual field image. On the image pickup surface, an object image in a side-view visual field is formed in an annular shape on an outer circumferential side of the front-view visual field image through the mirror lenses 15 facing the side-view observation window 13. The object image is acquired as a side-view visual field image.

Figure 4B:
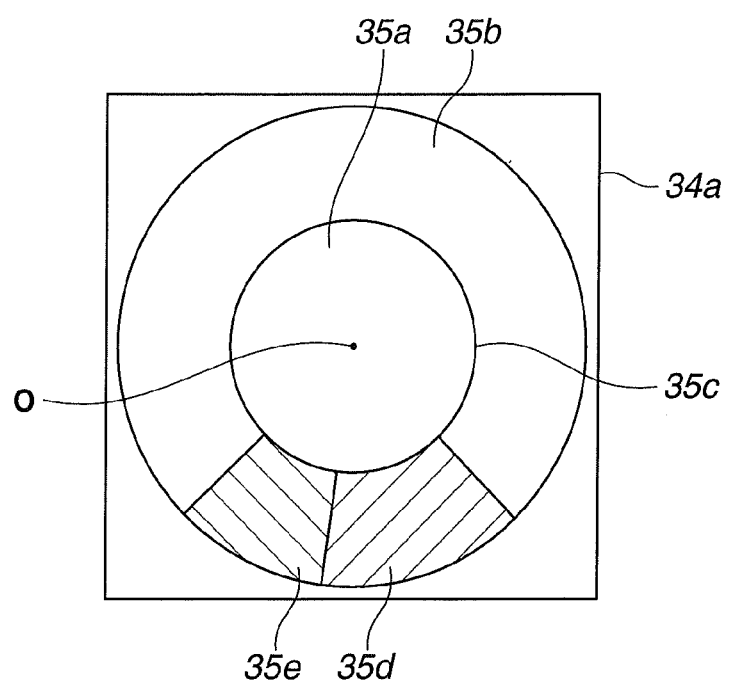
FIG. 4B is a diagram showing a circular region and an annular region in which a front-view object image and a side-view object image are respectively formed on an image pickup surface of an image pickup device.

FIG. 4B shows a circular region 35*a* and an annular region 35*b* in which a front-view object image and a side-view object image are respectively formed on an image pickup surface 34*a* of the image pickup device 34. A front-view object image passed through the distal end lens 41 of the front-view observation window 12 is formed in the circular region 35*a* in a center in a rectangular region of the image pickup surface 34*a*. A side-view object image passed through the mirror lenses 15 of the side-view observation window 13 is formed in the annular region 35*b* on an outer side of the circular region 35*a*. Reference sign 35*c* denotes a circular portion to be a boundary between the front-view object image and the side-view object image.

However, in the present embodiment, the region 35*d* is mechanically shielded by the supporting member 18 from the light from the object side made incident in the annular region 35*b*. The region 35*d* changes to a non-image pickup region in which an image is not picked up by the image pickup device 34. A region 35*e* may be shaded (masked) by, for example, signal processing to prevent a shaft portion of a treatment instrument projected from the channel distal end opening portion 17 from appearing in a visual field of the side-view observation window 13.

Note that, as shown in FIG. 4A, the mirror lenses 15 reflect the light from the object on the side twice and guide the light to the rear lens section 52 side to thereby form a front-view image and a side-view image on an outer circumferential side of the front-view image on the common image pickup surface 34*a* such that the images can be easily viewed.

On the other hand, when the front-view image and the side-view image are formed on the common image pickup surface 34*a* by being reflected once, a direction (an orientation) in the front-view image and a direction (an orientation) in the side-view image do not match and convenience for a user such as the surgeon is deteriorated. More specifically, a direction from a center to an outer circumferential side in the front-view image changes to a direction from an outer side to an inner side of a ring, i.e., an opposite direction rather than a direction from the inner side to the outer side of the ring.

On the other hand, in the present embodiment, structure for reflecting the light twice is adopted as explained above. Therefore, as it is also understood from FIG. 4A, the direction from the center to the outer circumferential side in the front-view image is the direction from the inner side to the outer side of the ring in the side-view image as well. The directions match to be the same direction. In other words, an object portion on the outer circumferential side in the front-view image appears in a position on the inner side of the side-view image. Therefore, the surgeon can perform an endoscopic examination in a state in which both the images are easily viewed.

Note that, since the treatment instrument is formed of a member having high reflectance, when the shaft portion of the treatment instrument is projected to the distal end side passing through the side-view visual field, the treatment instrument acts to reduce an amount of illumination light with a light-adjusting function (for adjusting the amount of illumination light according to detection of brightness of a video signal). Therefore, the shaft portion of the treatment instrument is shaded not to appear in the side-view observation visual field to prevent the amount of illumination light from being reduced when the light-adjusting function is actuated. The distal end side of the treatment instrument can be observed by the front-view visual field.

In the present embodiment, as shown in FIG. 3, side-view illumination light emitted from the side-view illumination window 14 side in a side surface direction is reflected by a reflection surface 21*a* and laterally emitted. However, the side-view illumination light is not emitted to the supporting member 18 side.

The side-view illumination windows 14 are provided in a plurality of places on an outer circumferential surface in a vicinity of a proximal end adjacent to the side-view observation window 13 in the cylindrical distal end portion 10. In the present embodiment, the side-view illumination windows 14 are provided in two places on both left and right sides in the circumferential direction as indicated by dotted lines in FIG. 3. The side-view illumination windows 14 emit the side-view illumination light to an entire region in the circumferential direction excluding a part on a lower portion side where the supporting member 18 is provided.

In FIG. 4A, a configuration for laterally emitting light emitted from a distal end face of one light guide 44. As shown in FIG. 4A, a distal end side of the light guide 44 functioning as a light emitting member arranged along a longitudinal direction of the distal end portion 6 is exposed on an end face of the side opening portion 64 at the proximal end of the cylindrical distal end portion 10.

The side-view illumination member 21 having the annular shape arranged in the side opening portion 64 reflects, on the reflection surface 21a having a concave surface shape in a reflection member 21b, the light emitted from the distal end face of the light guide 44. The side-view illumination member 21 reflects, on the reflection surface 21a having the concave surface shape, the light emitted from the distal end face of the light guide 44 to thereby emit the light as a side illumination light for illuminating the object in the side visual field. As shown in FIG. 4A, a concave surface portion is covered with a transparent member 21c to protect the reflection surface 21a not to be deteriorated.

In a longitudinal cross section shown in FIG. 4A, the reflection surface 21a is a concave surface or a concave surface having a substantially semispherical shape. The reflection surface 21a is formed longer than the distal end face of the light guide 44 along the circumferential direction of the cylindrical distal end portion 10.

The side-view illumination member 21 reflects, with the reflection surface 21a, light emitted from the distal end face (an emission end face) of the light guide 44 to the distal end side of the distal end portion 6 to change a traveling direction of the light to a side surface direction. The side-view illumination member 21 guides the light in the side surface direction in a wide range extending along the circumferential direction and emits the light from the side-view illumination window 14 to illuminate an observation visual field side (an observation target side) of the side-view observation window 13. The light emitted from the side-view illumination window 14 in the side surface direction is side-view illumination light.

As explained later, the side-view illumination member 21 having the annular shape is inserted from the side opening portion 64 and fixed, for example, in a state in which the side-view illumination member 21 is divided into two to left and right.

The reflection surface 21a in the reflection member 21b forming the side-view illumination member 21 can be formed by providing a metal thin film of aluminum, chrome, nickel chrome, silver, gold, or the like on an inner side surface of the reflection member 21b.

As shown in FIG. 4A and the like, the mirror lenses 15 in the front lens section 51 has a large outer diameter (an outer diameter substantially the same as an outer diameter of the cylindrical distal end portion 10). Therefore, when a method of assembling the image pickup unit 60 by inserting the front lens section 51 from the rear opening portion 62 as in an assembly method in the past is adopted, it is necessary to set an inner diameter of the rear opening portion 62 equal to or larger than the outer diameter of the mirror lens 15. Therefore, an outer diameter of the distal end portion 6 is large.

Therefore, in the present embodiment, an assembly method explained below is adopted.

An assembly method for the image pickup unit 60 according to the present embodiment is an assembly method for an endoscope image pickup unit including the main body portion 61 functioning as the distal end portion main body portion including the front opening portion 63, the side opening portion 64, and the rear opening portion 62 functioning as opening portions respectively opened to a front, a side, and a rear and the arrangement space portion 65 that communicates with the three opening portions, the front lens section 51 functioning as a lens section including the distal end lens 41 having an outer diameter that generally fits in the front opening portion 63, and the image pickup section 55 that fits in the rear opening portion 62 and includes the image pickup device 34 arranged in an image forming position by the lens section and the rear lens section 52 arranged to be integrated with the image pickup device 34 in a rear of the lens section. The assembly method includes an inserting step for inserting the lens section into the arrangement space portion 65 from the side opening portion 64, a fitting step for fitting the lens section, which is inserted into the arrangement space portion 65, in the front opening portion 63 that communicates with the arrangement space portion 65, and an image pickup section fitting step for fitting the image pickup section 55 in the rear opening portion 62 from a rear of the rear opening portion 62.

By adopting this method, even when the rear opening portion 62 having an inner diameter smaller than an outer diameter of the lens section is used, it is possible to assemble the image pickup unit 60 without increasing the outer diameter of the distal end portion 6. Further, it is possible to provide the endoscope 2 including the image pickup unit 60 assembled by such an assembly method.

The endoscope according to the present embodiment includes the image pickup unit 60 manufactured by the assembly method.

The endoscope 2 according to the present embodiment includes the image pickup unit 60 including the main body portion 61 functioning as the distal end portion main body portion including the front opening portion 63, the side opening portion 64, and the rear opening portion 62 functioning as opening portions respectively opened to a front, a side, and a rear and the arrangement space portion 65 that communicates with the three opening portions, the front lens section 51 functioning as a lens section including the distal end lens 41 having an outer diameter that generally fits in the front opening portion 63, and the image pickup section 55 that fits in the rear opening portion 62 and includes the image pickup device 34 arranged in an image forming position by the lens section or the image pickup device 34 arranged in an image forming position by the lens section and the rear lens section 52 arranged to be integrated with the image pickup device 34 in a rear of the lens section. The side opening portion 64 is opened having an area equal to or larger than an area of projection to a side of the lens section to enable the lens section to be inserted from the side and opened having an area smaller than an area of projection to the side of the lens section and the image pickup section after assembly, and the rear opening portion 62 is opened having an inner diameter smaller than a maximum outer diameter of the lens section and substantially the same as an outer diameter of the image pickup section 55.

The assembly method for the image pickup unit 60 according to the present embodiment is explained with reference to FIG. 5 and FIGS. 6A to 6E.

Figure 5:
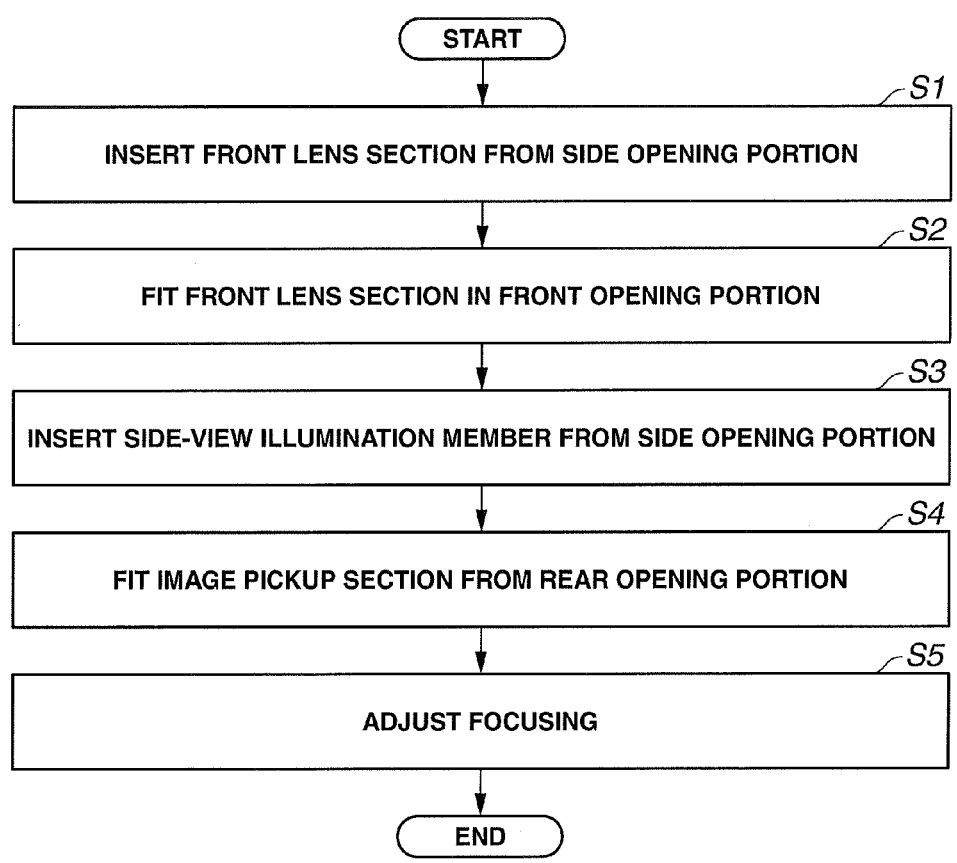
FIG. 5 is a flowchart for explaining a procedure of an assembly method for an image pickup unit according to the first embodiment of the present invention.
Figure 6A:
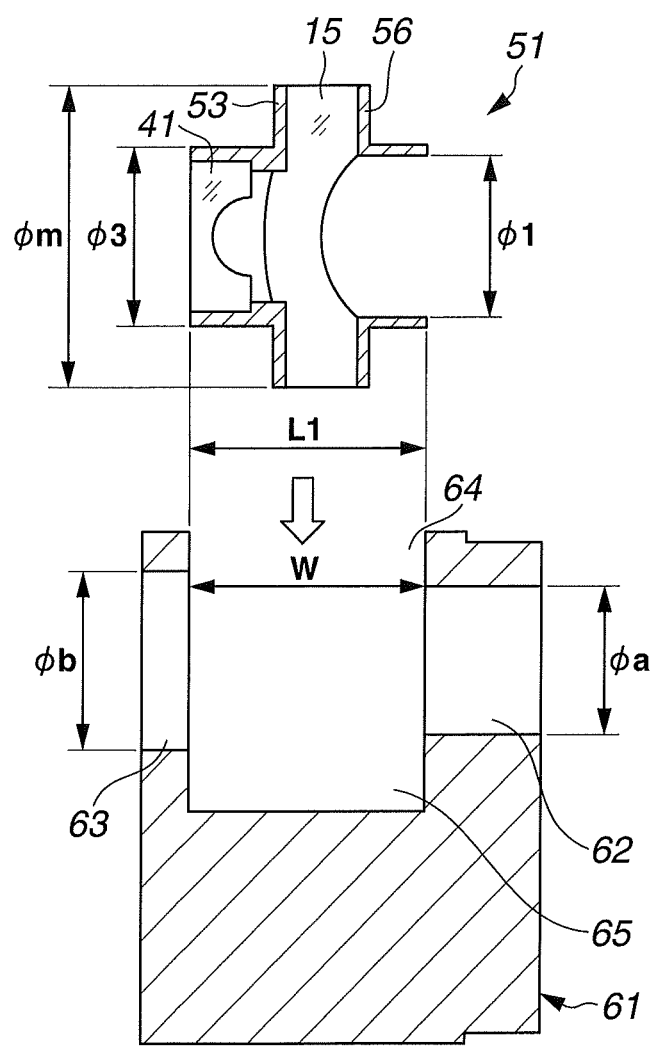
FIG. 6A is a diagram showing a situation in which a lens section is inserted into an arrangement space portion from a side opening portion.

First, as shown in step S1 of FIG. 5, the front lens section 51 is inserted into the arrangement space portion 65 from the side opening portion 64. FIG. 6A shows a situation of an inserting step in step S1.

As shown in FIG. 6A, when an inner diameter of the rear opening portion 62 is represented as $\phi a$, an inner diameter of the lens frame 56 is represented as $\phi 1$, an outer diameter of the lens frame 54 of the image pickup section 55 is represented as $\phi 2$ (see FIG. 6D), and an inner diameter of the front opening portion is represented as ϕb, in the present embodiment, the inner diameters and the outer diameter are set to a condition ϕ1>ϕa=ϕ2.

The front opening portion 63 and the rear opening portion 62 in the main body portion 61 are machined to be coaxial such that center axes of openings coincide with each other.

The inner diameter ϕb of the front opening portion 63 is the same as the outer diameter ϕ3 on a distal end side of the lens frame 53 of the front lens section 51 (ϕb=ϕ3). The front lens section 51 is inserted to be fitted in the front opening portion 63 and the lens frame 54 of the image pickup section 55 is inserted to be fitted in the rear opening portion 62, whereby it is possible to cause (adjust) optical axes of the front lens section 51 and the image pickup section 55 to coincide with each other. The distal end lens 41 has an outer diameter that fits in an inner diameter on the distal end side of the lens frame 53. Therefore, the outer diameter is slightly smaller than the inner diameter of the front opening portion 63 and is an outer diameter size that generally fits in the front opening portion 63.

Note that opening length W in the longitudinal direction of the distal end portion 6 in the side opening portion 64 is set to a size equal to or larger than length L1 in an optical axis direction of the front lens section 51 (W≧L1). The side opening portion 64 is opened having the opening length W in the circumferential direction excluding a lower end. Therefore, it is possible to insert the front lens section 51 into the arrangement space portion 65 from the side opening portion 64.

Therefore, the side opening portion 64 is laterally opened having a size equal to or larger than the size (dimensions) of an area of projection to the side of the front lens section 51 to enable the front lens section 51 to be inserted into the side opening portion 64 from a side orthogonal to the optical axis direction of the front lens section 51. In the present embodiment, the side opening portion 64 is laterally opened having a size smaller than the size of an area of projection to the side of the front lens section 51 and the image pickup section 55 after assembly.

In other words, the side opening portion 64 is not laterally opened having a size enough for enabling the integrated front lens section 51 and the image pickup section 55 after the assembly of the front lens section 51 and the image pickup section 55 to be inserted from the side opening portion 64. More plainly, length in a longitudinal direction of the integrated front lens section 51 and the image pickup section 55 is larger than the opening length W on the side of the side opening portion 64. Therefore, it is impossible to insert the front lens section 51 and the image pickup section 55 after assembly into the arrangement space portion 65 from the side opening portion 64.

The arrangement space portion 65 has a columnar arrangement space substantially equal to the length W and an outer diameter ϕm of the mirror lenses 15 centering around a center axis of the front opening portion 63 and the rear opening portion 62. The outer diameter ϕm of the mirror lenses 15 is equal to a maximum outer diameter of the lens frame 53 and the lens frame 56.

Note that, in FIG. 6A and the like, a situation in which the front lens section 51 is inserted into the arrangement space portion 65 from the side opening portion 64, which is on an upper side on a paper surface of the figures. However, the front lens section 51 can also be inserted from a side perpendicular to the paper surface.

Figure 6B:
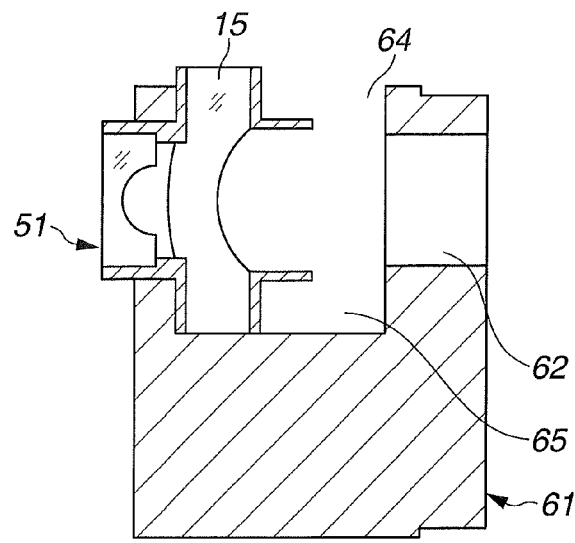
FIG. 6B is a diagram showing a situation in which the inserted lens section is fitted in a front opening portion.

Subsequently, as shown in step S2 of FIG. 5, the front lens section 51 inserted into the arrangement space portion 65 is moved to a front side in the arrangement space portion 65 to fit the distal end lens 41 of the front lens section 51 in the front opening portion 63. FIG. 6B shows a situation in which the front lens section 51 is fitted in the front opening portion 63 according to a fitting step in step S2.

Subsequently, as shown in step S3 of FIG. 5, the side-view illumination member 21 is inserted into the arrangement space portion 65 from the side opening portion 64 and fitted and arranged in the lens frame 56.

Figure 6C:
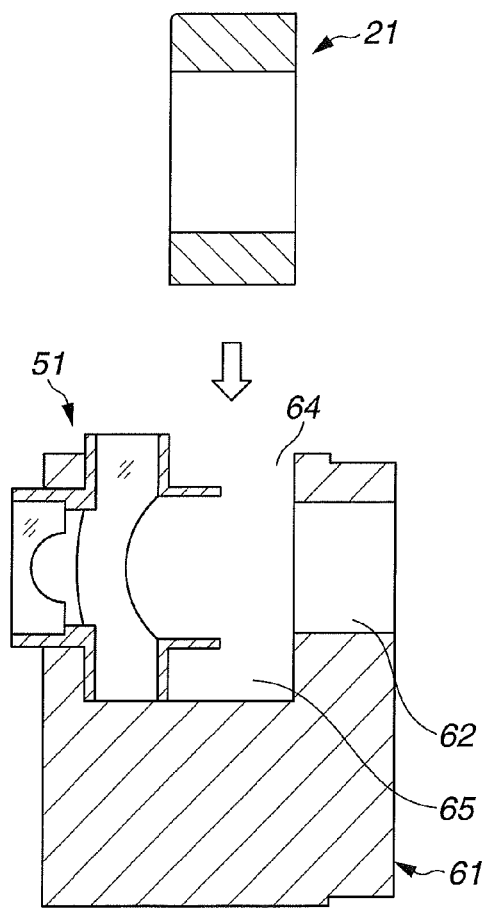
FIG. 6C is a diagram showing a situation in which a side-view illumination member is inserted into the arrangement space portion from the side opening portion.

FIG. 6C shows a situation in which the side-view illumination member 21 is inserted into the arrangement space portion 65 according to an arranging step in step S3. In this case, as explained above, the side-view illumination member 21 having the annular shape is inserted into the arrangement space portion 65 in a state in which the ring is divided into, for example, two (because the side-view illumination member 21 cannot be inserted while keeping in the annular shape). After being fitted and arranged in the lens frame 56, the side-view illumination member 21 is bonded into the annular shape by an adhesive or the like.

Figure 6D:
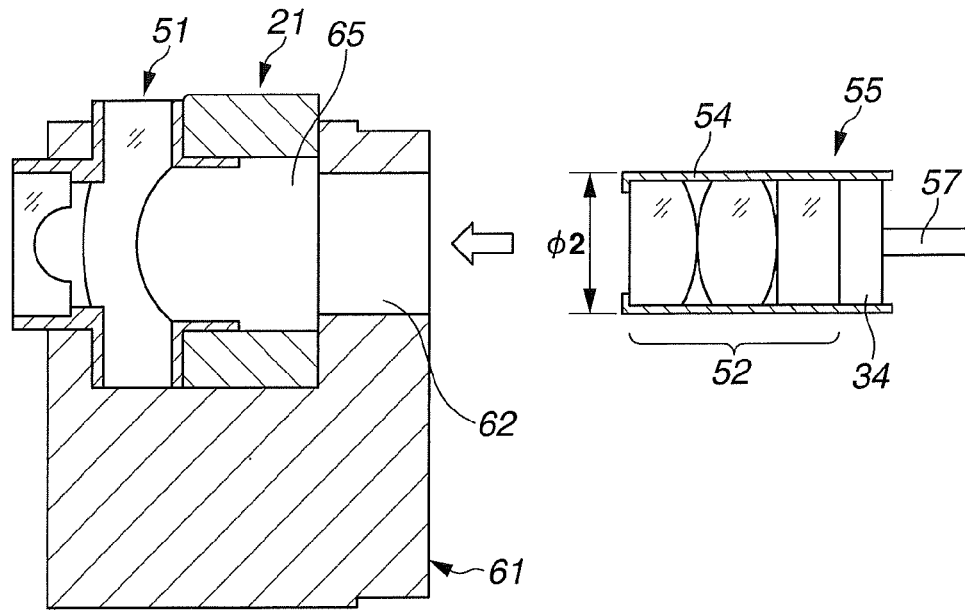
FIG. 6D is a diagram showing a situation in which an image pickup section is inserted into the arrangement space portion from a rear opening portion.

Subsequently, as shown in step S4 of FIG. 5, a distal end side of the image pickup section 55 is inserted into the arrangement space portion 65 from the rear opening portion 62 to fit the lens frame 54 of the image pickup section 55 in the inner diameter of the rear opening portion 62. FIG. 6D shows a situation in which the distal end side of the image pickup section 55 is inserted into the arrangement space portion 65 from the rear opening portion 62 in a fitting step in step S4.

As explained above, the front opening portion 63 and the rear opening portion 62 are formed to be coaxial. Therefore, the image pickup section 55 is inserted from the rear of the rear opening portion 62 and fitted in the rear opening portion 62, whereby an optical axis of the front lens section 51 and an optical axis of the rear lens section 52 coincide with each other.

Subsequently, adjustment of focusing in step S5 of FIG. 5 is performed. The lens frame 54 of the image pickup section 55 fitted in the rear opening portion 62 is moved in an optical axis O direction to perform adjustment of focusing to form, in a focus state with respect to an object in a predetermined distance, an image of the object on a front side of the front opening portion 63 (the front-view observation window 12) and an image of the object on a lateral side of the front opening portion 63 on the image pickup surface 34a of the image pickup device 34.

The lens frame 54 is fixed in the rear opening portion 62 of the main body portion 61 in a focused fitting position. The lens frame 53 is also fixed to the front opening portion 63 of the main body portion 61 with an adhesive, fixing screws, or the like. The adhesive or the like is filled in a space around the lens frame 56 to complete the assembly of the image pickup unit 60.

Figure 6E:
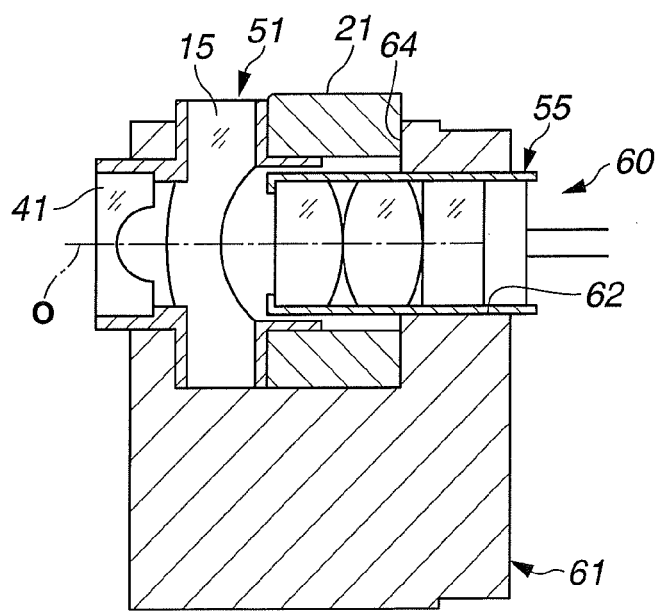
FIG. 6E is a diagram showing a state in which the inserted image pickup section is fitted in the rear opening portion.

FIG. 6E shows the image pickup unit 60 for which assembly is completed after a focusing step in step S5 is performed.

Figure 7A:
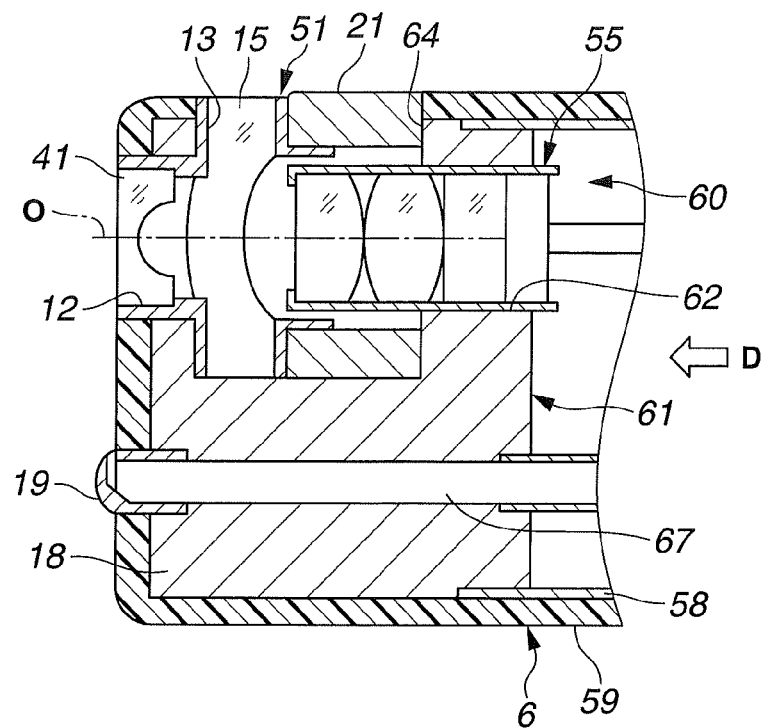
FIG. 7A is a longitudinal sectional view showing structure of a vicinity of the assembled distal end portion.

Note that the image pickup unit 60 assembled in this way further undergoes work for integrating the image pickup unit 60 on the distal end side of the insertion portion 4 to have a configuration shown in FIGS. 2, 3, and 7A. Note that FIG. 7A shows a sectional structure around the main body portion in a cross section position same as a cross section position shown in FIGS. 6A to 6E. The cross section position corresponds to an A-O-C cross section in FIG. 3. Note that, in FIGS. 6A to 6E, a conduit 67 that communicates with the nozzle portion for front-view observation window 19 in the supporting member 18 shown in FIG. 7A is omitted (the same applies in FIGS. 9A to 9G referred to below).

Figure 7B:
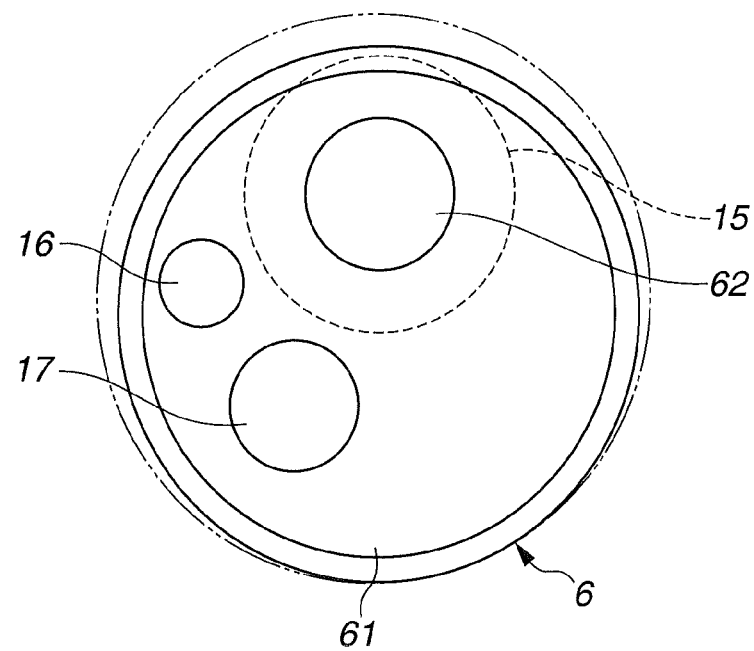
FIG. 7B is a rear view of the distal end portion viewed from a D direction in FIG. 7A.

FIG. 7B shows a rear view of the image pickup unit 60 viewed from a D direction in FIG. 7A. In the assembly method according to the present embodiment explained above, the inner diameter of the rear opening portion 62 is set smaller than the outer diameter of the mirror lens 15 of the front lens section 51 and same as the outer diameter of the image pickup section 55. Therefore, it is possible to reduce the outer diameter of the distal end portion 6.

Therefore, with the assembly method according to the present embodiment, even when the outer diameter of the front lens section 51, which configures the objective lens system 11, is larger than the outer diameter of the image pickup section 55, it is possible to reduce the outer diameter size of the distal end portion 6.

On the other hand, when the assembly method according to the present embodiment is not adopted and the assembly method of the laid-open patent application explained above is adopted, the inner diameter of the rear opening portion 62 needs to be set to be equal to or larger than the outer diameter of the mirror lens 15 indicated by a dotted line in FIG. 7B. Therefore, it is necessary to set the distal end portion 6 to a larger outer diameter as indicated by an alternate long and two short dashes line.

As explained above, with the assembly method for the image pickup unit 60 according to the present embodiment, the outer diameter of the distal end portion 6 can be reduced in size. With the endoscope 2 in which the image pickup unit 60 assembled by the assembly method is mounted at the distal end portion 6, since the outer diameter of the distal end portion 6 is small, when the insertion portion 4 is inserted into a body cavity of a patient, the insertion portion 4 can be more smoothly inserted. Therefore, the surgeon can perform an endoscopic examination and, when necessary, treatment by the treatment instrument smoothly and in a short time.

In the structure of the image pickup unit 60 according to the present embodiment, a front-view object image and a side-view object image are formed on the common image pickup device 34 to be concentric. The front-view object image and the side-view object image are reflected twice by the mirror lens 15 and formed such that a direction from a center to an outer circumference of the front-view object image can be maintained in the side-view object image as well.

Therefore, with the endoscope 2 according to the present embodiment, when an image picked up by the image pickup unit 60 is displayed as front-view and side-view images, the surgeon can easily grasp both the images and can more smoothly perform diagnosis and the like. Therefore, it is possible to improve convenience for the surgeon. Note that, in the first embodiment, the lens frame 56 does not have to be provided.

(Second Embodiment)

A second embodiment of the present invention is explained. Since the present embodiment is similar to the first embodiment, differences are explained. In the first embodiment, the condition φ1>φa=φ2 (when the lens frame 56 is not provided as explained above, φa=φ2) is set. However, in the present embodiment, assembly is possible under a condition different from such a condition. More specifically, assembly is possible under a condition φ2=φ1<φa=φ1'. φ1' represents an outer diameter on a rear end side of the lens frame 56.

In the present embodiment, before assembly, the lens frame 56 separated from the front lens section 51 is used. Length L2 in the optical axis direction of the lens frame 56 is set longer than the length L2 in the case of the first embodiment.

However, the length L2 is set to equal to or smaller than the opening length W of the side opening portion 64 to enable the lens frame 56 to be inserted into the arrangement space portion 65 from the side opening portion 64. Note that, in the present embodiment, a front lens section in a state in which the lens frame 56 is separated is denoted by a reference numeral 51'.

FIG. 8 shows a procedure of an assembly method for the image pickup unit 60 according to the present embodiment. FIGS. 9A to 9F show explanatory diagrams of the assembly method.

Figure 9A:
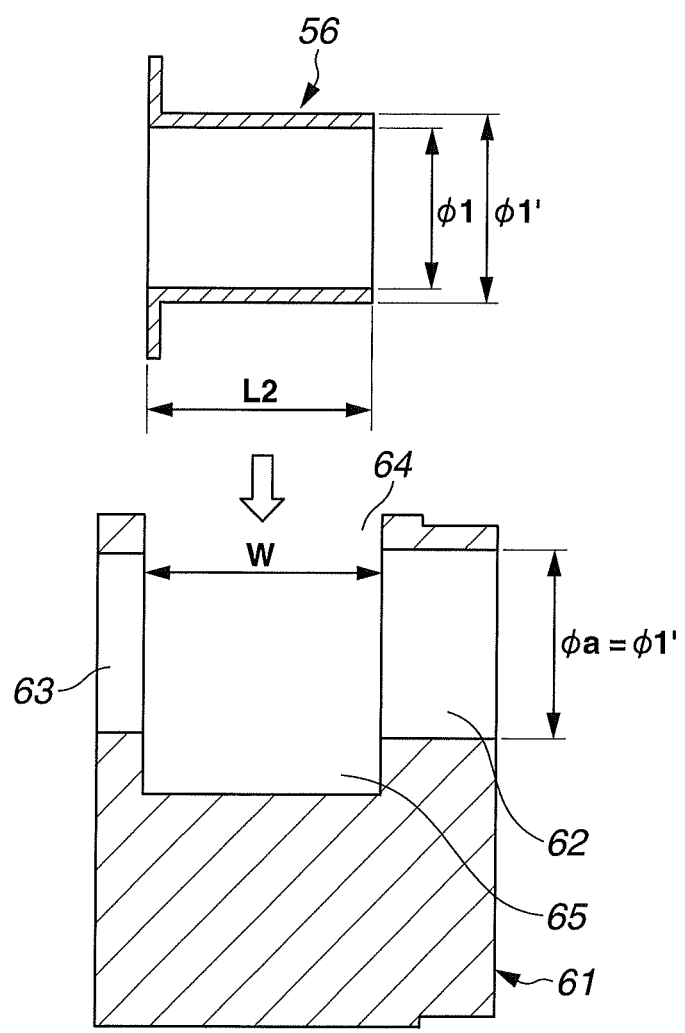
FIG. 9A is a diagram showing a situation in which a lens frame is inserted into an arrangement space portion from a side opening portion.

In the procedure of the assembly method shown in FIG. 8, as first step S11, the lens frame 56 separated from the front lens section 51' is inserted into the arrangement space portion 65 from the side opening portion 64. FIG. 9A shows a situation in which the lens frame 56 is inserted into the arrangement space portion 65 from the side opening portion 64.

In next step S12, after the inserted lens frame 56 is fitted in the rear opening portion 62, the front lens section 51' is inserted into the arrangement space portion 65 from the side opening portion 64.

Figure 9B:
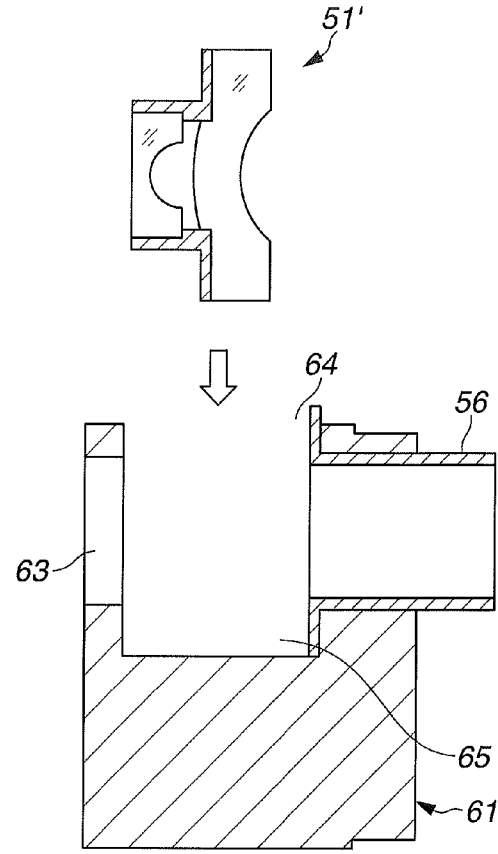
FIG. 9B is a diagram showing a situation in which a front lens section is inserted into the arrangement space portion from a side opening portion in a state in which the lens frame is fitted in a rear opening portion.

FIG. 9B shows a situation in which the front lens section 51' is inserted into the arrangement space portion 65 from the side opening portion 64 in a state in which the lens frame 56 is fitted in the rear opening portion 62.

In next step S13, the front lens section 51' inserted into the arrangement space portion 65 is fitted in the front opening portion 63. Step S13 is the same as step S2 of FIG. 5.

Figure 9C:
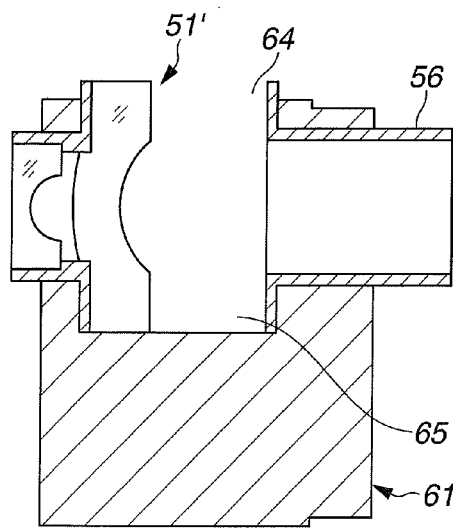
FIG. 9C is a diagram showing a state in which the front lens section is fitted in a front opening portion.

FIG. 9C shows a state in which the front lens section 51' is fitted in the front opening portion 63.

Figure 9D:
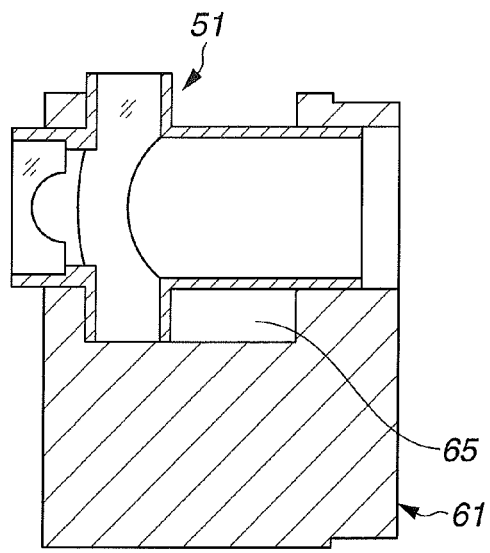
FIG. 9D is a diagram showing a state in which the lens frame is fixed to a rear surface of front lens section.

In next step S14, the lens frame 56 is moved forward and a front surface of the lens frame 56 is fixed to a rear surface of the front lens section 51' with an adhesive or the like. FIG. 9D shows a state in which the lens frame 56 is fixed to the rear surface of the front lens section 51' (i.e., a state in which the front lens section 51 is fitted in the front opening portion 63).

Figure 9E:
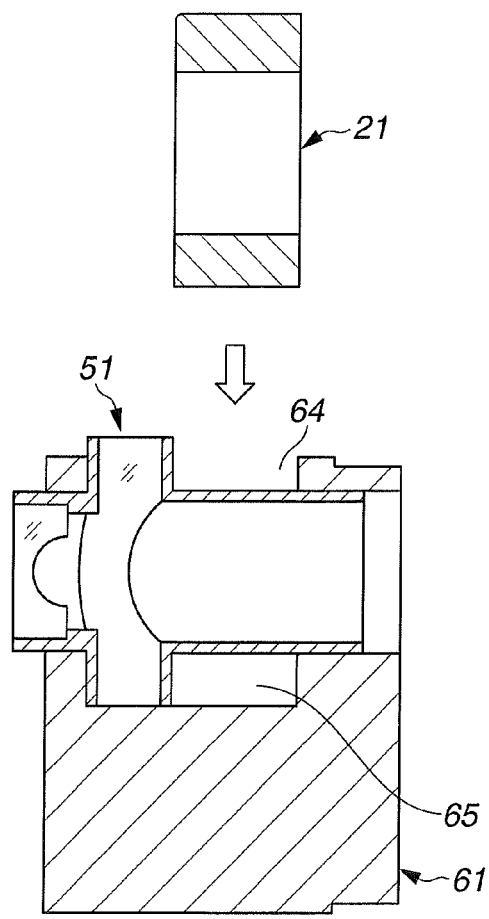
FIG. 9E is a diagram showing a situation in which a side-view illumination member is inserted from the side opening portion.

In next step S15, the side-view illumination member 21 is inserted from the side opening portion 64 and arranged and fixed on an outer circumferential surface of the lens frame 56. FIG. 9E shows a situation in which the side-view illumination member 21 is inserted from the side opening portion 64.

Figure 9F:
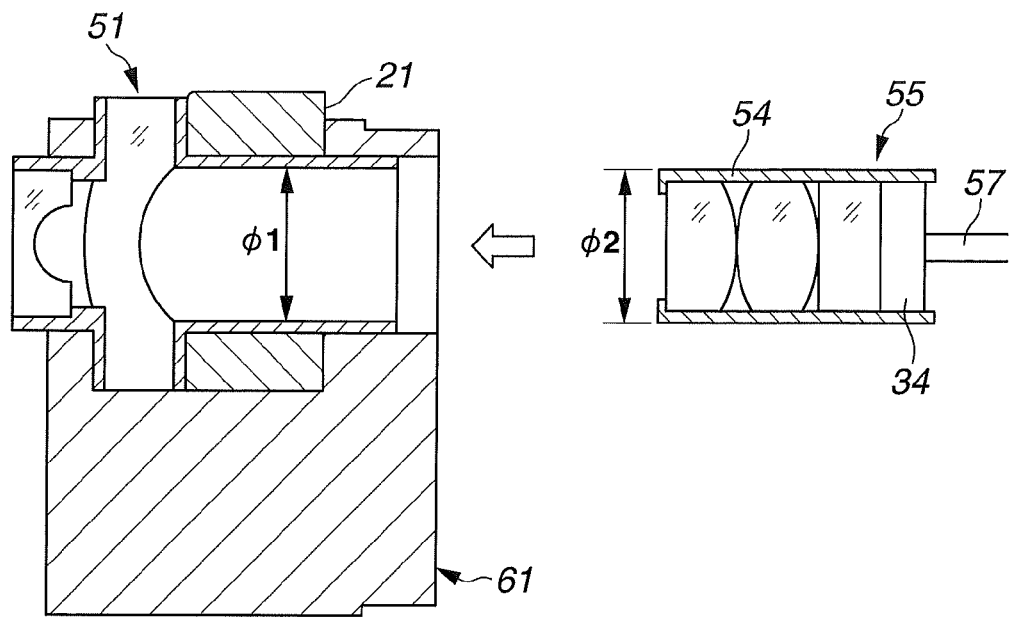
FIG. 9F is a diagram showing a situation in which an image pickup section is inserted into an arrangement space portion side from a rear of the rear opening portion.

In next step S16, the image pickup section 55 is inserted from the rear of the rear opening portion 62. The inserted image pickup section 55 is fitted in the lens frame 56. FIG. 9F shows a situation in which the image pickup section 55 is inserted from the rear of the rear opening portion 62.

In next step S17, adjustment of focusing for the front lens section 51 and the image pickup section 55 is applied to the image pickup section 55 fitted in the lens frame 56. The lens frame 54 of the image pickup section 55 fitted in the lens frame 56 is moved in the optical axis O direction to perform the adjustment of focusing to form, in a focus state in a predetermined distance, an image of an object on a front side and an image of the object on a lateral side on the image pickup surface 34a of the image pickup device 34.

The image pickup section 55 is fixed in the lens frame 56 in a fitting position of the image pickup section 55 fitted in the lens frame 56 in a focused state. The lens frame 56 is also fixed to the main body portion 61 to complete the assembly shown in FIG. 8.

Figure 9G:
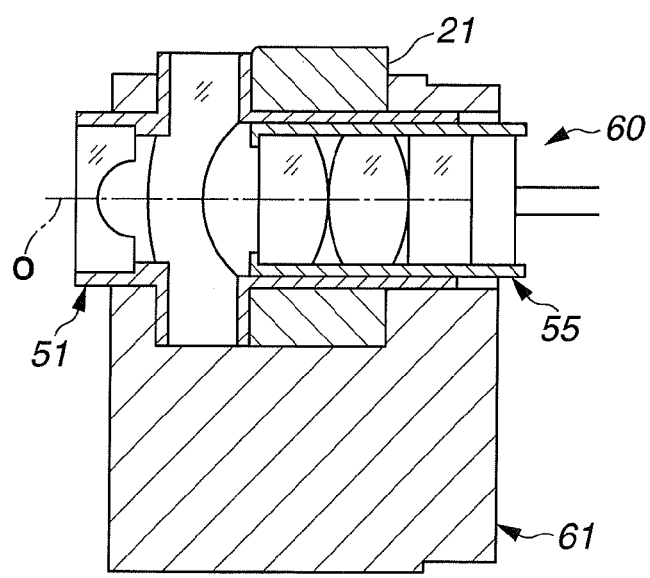
FIG. 9G is a diagram showing the image pickup unit for which assembly is completed by a focusing step.

FIG. 9G shows the image pickup unit 60 for which the assembly is completed according to a focusing step in step S17.

Figure 10:
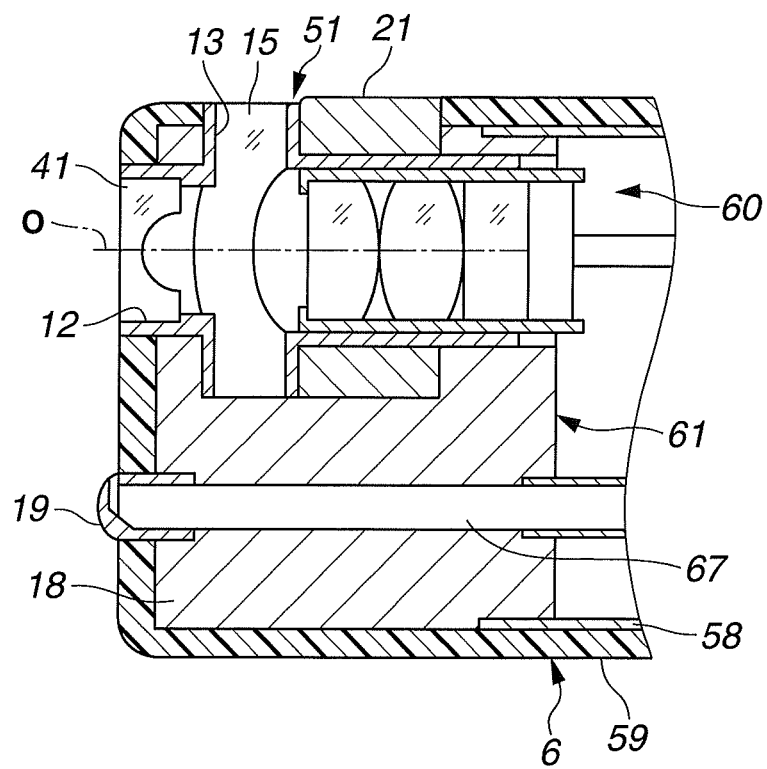
FIG. 10 is a longitudinal sectional view showing structure of a vicinity of an assembled distal end portion.

The image pickup unit 60 further undergoes work for integrating the image pickup unit 60 on the distal end side of the insertion portion 4 to have structure shown in FIG. 10.

Note that FIG. 10 shows sectional structure around the main body portion in a cross section position same as the cross section position shown in FIGS. 9A to 9G.

In this embodiment, as in the first embodiment, the image pickup section 55 is inserted from the rear opening portion 62 and fitted in the lens frame 56, whereby optical axes of the front lens section 51 and the rear lens section 52 of the image pickup section 55 coincide with each other. Therefore, it is possible to easily assemble the image pickup unit 60 only by performing the adjustment of focusing in the optical axis direction. In this embodiment, as in the first embodiment, the image pickup unit 60 can be assembled using the rear opening portion 62 having the inner diameter smaller than the outer diameter of the mirror lens 15. Therefore, the outer diameter of the distal end portion 6 can be small.

In the first embodiment, an air gap portion is present between the lens frame 56 and the lens frame 54. In this embodiment, the lens frame 56 and the lens frame 54 are fitted into each other and the side-view illumination member 21 is fitted in an outer circumference of the lens frame 54 to eliminate the air gap portion. Therefore, water tightness of a lens section on an inner side of the lens frames 56 and 54 can be improved.

Note that, in the embodiments explained above, the objective lens system 11 functioning as an image forming lens system that forms an image on the image pickup device 34 is configured by the front lens section 51 functioning as a lens section and the rear lens section 52 provided integrally with the image pickup section 55. However, the objective lens system 11 is not limited to this configuration. The objective lens system 11 can be applied as well in a configuration in which, for example, a lens of the rear lens section 52 is provided on the front lens section 51 side to form a lens section and only the image pickup device 34 is provided in the image pickup section 55. In this case, focusing is performed such that the image pickup device 34 of the image pickup section 55 is located in an image forming position of (a lens system by) the lens section.

An image pickup unit may be assembled according to a modification of the second embodiment explained below.

In the embodiments explained above, the distal end lens 41 and the mirror lens 15 are integrally attached to the front lens section 51' or the front lens section 51. Therefore, when an image pickup unit that can observe a front view and a side view is assembled only as one type, it is possible to reduce man-hour.

On the other hand, if observation ranges of a front view and a side view can be changed or a focus distance is changed in a front view and a side view to perform observation (image pickup), it is possible to improve options and convenience for a user.

Therefore, in the present modification, the front lens section 51' in the second embodiment is configured by a front lens section 51" (see FIG. 11B) including the mirror lens 15 and the lens frame 53 and a distal end lens section 69 (see FIG. 11C) including a lens frame 68 that fits in the lens frame 53 and the distal end lens 41. In this case, an outer diameter of a distal end of the lens frame 53 fits in an inner diameter of the front opening portion 63.

Figure 11A:
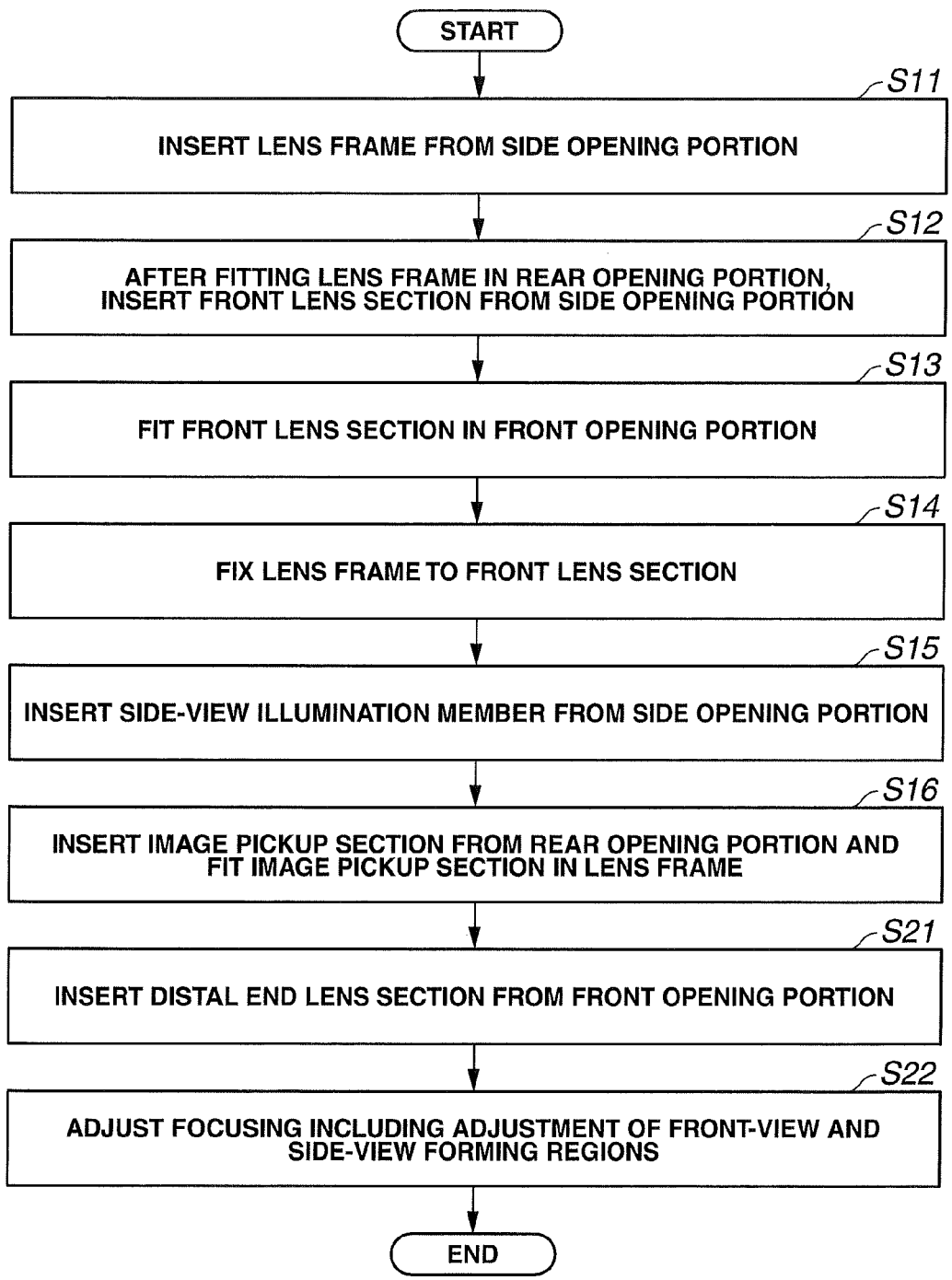
FIG. 11A is a flowchart for explaining a procedure of an assembly method for an image pickup unit according to a modification of the second embodiment.

The image pickup unit is assembled according to a procedure shown in FIG. 11A. Steps S11 to S16 in the procedure shown in FIG. 11A are the same as steps S11 to S16 in FIG. 8 in which the front lens section 51' is read as the front lens section 51".

Figure 11B:
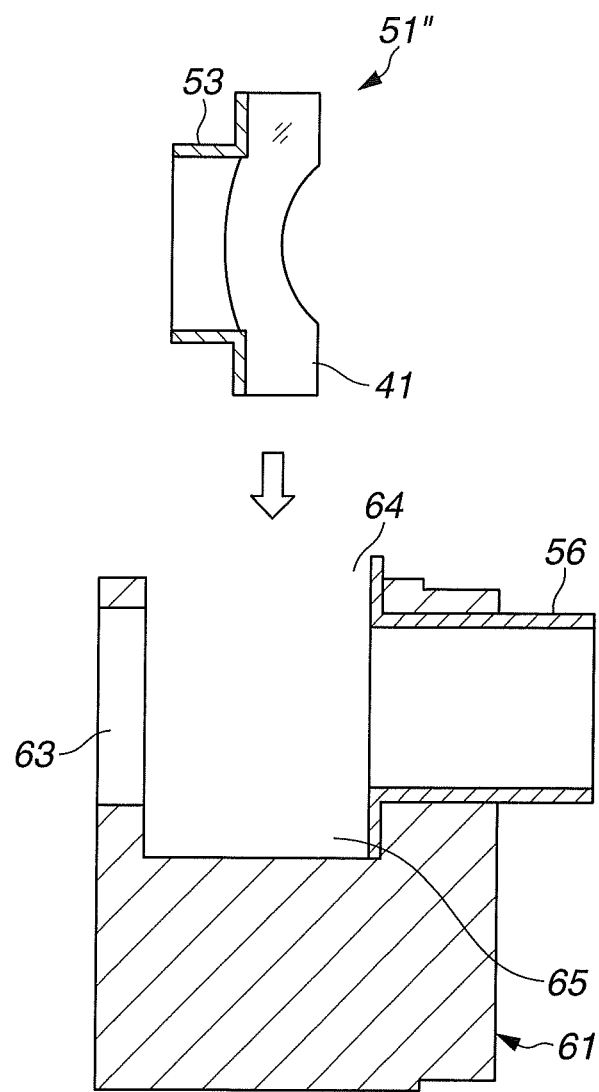
FIG. 11B is a diagram showing a situation in which a front lens section is inserted into an arrangement space portion from a side opening portion.

A figure corresponding to, for example, step S12 in FIG. 11A is like FIG. 11B.

After step S16, in step S21, the lens frame 68 of the distal end lens section 69 is inserted from a front of the front opening portion 63 and fitted in the lens frame 53.

Figure 11C:
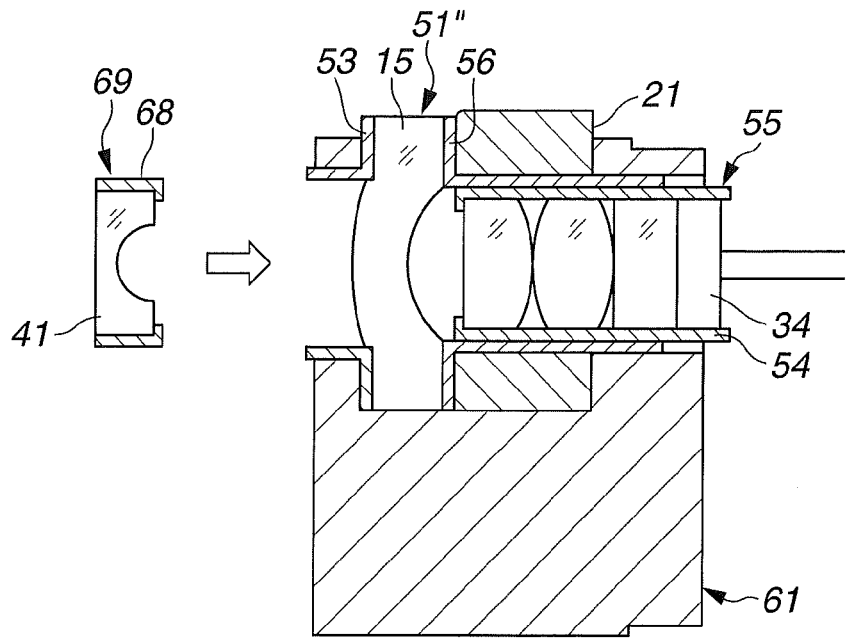
FIG. 11C is a diagram showing a situation in which a distal end lens section is inserted from a front opening portion side to be fitted in a lens frame of the front lens section.

FIG. 11C shows a situation in which the lens frame 68 of the distal end lens section 69 is inserted from the front of the front opening portion 63.

In next step S22, adjustment of a front-view image forming region and a side-view image forming region and adjustment of focusing are performed. Adjustment is also performed such that boundaries of the front-view image forming region and the side-view image forming region substantially coincide with each other.

As the adjustment, adjustment for moving the lens frame 54 of the image pickup section 55 in an optical axis direction with respect to the lens frame 56 (and adjustment of the side-view image forming region and adjustment of focusing of a side-view object image to a focus state by the movement adjustment) and adjustment for moving the lens frame 68 of the distal end lens section 69 in the optical axis direction with respect to the lens frame 53 (and adjustment of the front-view image forming region and adjustment of focusing of a front-view object image to the focus state by the movement adjustment) are performed. By performing such adjustment, it is possible to adjust the front-view image forming region and the side-view forming region, adjust focusing of the front-view object image and the side-view object image, and adjust the boundaries of the front-view image forming region and the side-view image forming region to substantially coincide with each other. In other words, after the adjustment of focusing of one object image to the focus state, it is possible to perform, while maintaining the focused state of the object image, the adjustment of focusing to set the other object image to the focus state. For example, after the adjustment of focusing of the side-view object image to the focus state, it is desirable to perform the adjustment of focusing of the front-view object image to the focus state according to the movement adjustment of the lens frame 68 of the distal end lens section 69 in the optical axis direction.

When the adjustment is performed as explained above, the respective object images are easily set to be able to be formed in the focus state. Even when a focus distance is changed in a front view and a side view or there is fluctuation in dimensions among products, it is possible to perform the adjustment to absorb the fluctuation and have a predetermined image forming characteristic.

In a state after the adjustment, the lens frames 68 and 54 and the like are fixed to complete the assembly of the image pickup unit 60. Further, work for integrating the assembled image pickup unit 60 on the distal end side of the insertion portion is performed.

According to the present modification, it is possible to observe a front view and a side view. The present modification can be applied in the case of an image pickup unit in which optical characteristics of the front view and the side view are different. Besides, the present modification has effects same as the effects of the second embodiment. The present modification is not limited to the procedure for performing step S21 after step S16 in FIG. 11A. Step S21 may be performed after step S14 or after step S15. The present modification may be applied to the first embodiment.

In the image pickup unit 60 assembled according to the embodiments explained above, the front lens section 51 and the like may be configured as explained below.

Figure 12:
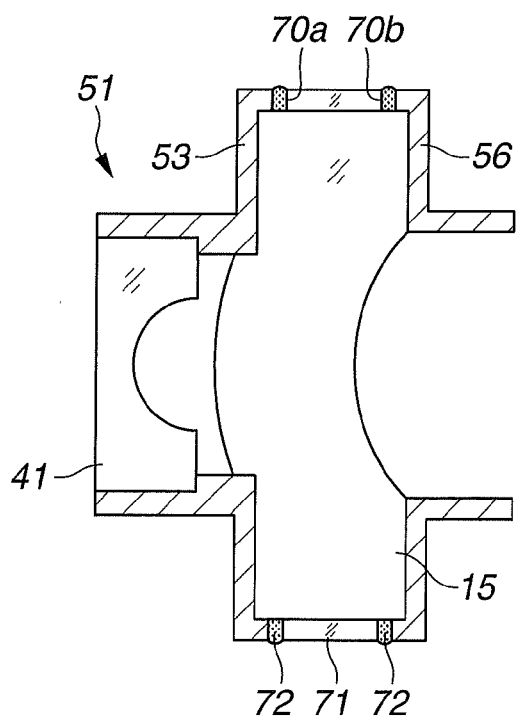
FIG. 12 is an explanatory diagram for explaining structure in which air tightness of an outer circumferential surface of a mirror lens is improved using a sapphire ring.

For example, the mirror lenses 15 that configure the front lens section 51 in the first embodiment explained above are formed in structure in which the outer circumferential surfaces of the mirror lenses 15 are exposed to the side-view observation window 13. However, as shown in FIG. 12, for example, the outer circumferential surface of the mirror lens 15 may be formed in higher airtight structure using a sapphire ring 71 including sapphire having a high airtight function.

An inner circumferential surface of the sapphire ring 71, in which metalize portions 70a and 70b obtained by subjecting both ends of a ring shape to metalize treatment (for enabling soldering) are formed, is joined to the outer circumferential surface of the mirror lens 15 glass-molded by using glass.

The sapphire ring 71 has length in an optical axis direction slightly smaller than length in the optical axis direction on the outer circumferential surface of the mirror lens 15. End faces on which the metalize portions 70a and 70b are formed in the sapphire ring 71 are opposed to, across a small air gap, the lens frames 53 and 56 formed by a metal member that cover both ends of the outer circumferential surface of the mirror lens 15.

The end faces of the metalize portions 70a and 70b and the lens frames 53 and 56 are subjected to soldering 72 in a small air gap portion to form the outer circumferential surface of the mirror lens 15 in airtight structure to prevent vapor from intruding into the mirror lens 15.

By adopting such airtight structure, it is possible to prevent vapor from intruding into the mirror lens 15 in a long-term use as well. It is possible to effectively prevent a blur of a visual field (due to vapor) of the side-view observation window 13 and the like.

Note that a configuration shown in FIG. 12 can be applied to the second embodiment as well. In this case, the soldering of the end face of the metalize portion 70b and the lens frame 56 only has to be performed in step S14 in FIG. 8.

Figure 13:
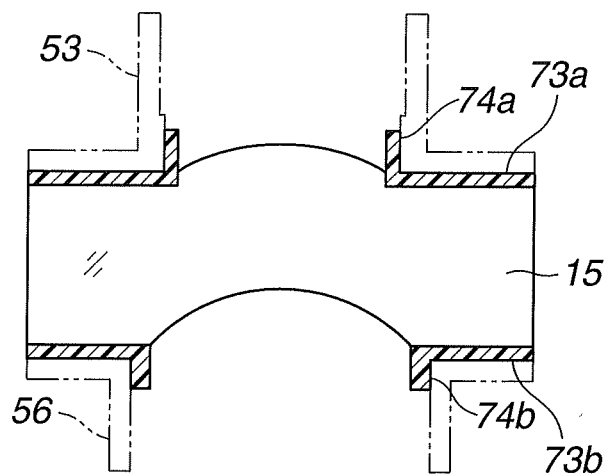
FIG. 13 is an explanatory diagram for explaining structure in which a resin-molded portion for positioning and attaching the lens frame simultaneously with molding of the mirror lens is provided.

In FIG. 13, when the mirror lens 15 is molded, the lens frames 53 and 56 explained above are further attached to front and rear surfaces (in FIG. 13, upper and lower surfaces) of the mirror lens 15. Resin-molded portions 73a and 73b having a function of positioning means for determining attachment positions of the lens frames 53 and 56 are formed by two-color molding.

Note that the resin-molded portions 73a and 73b are provided in portions on an outer side of an effective diameter of the mirror lens 15. The lens frames 53 and 56 are respectively fitted in and attached to positioning portions 74a and 74b by the resin-molded portions 73a and 73b as indicated by alternate long and two short dashes lines.

By adopting such structure, it is possible to omit adjustment for centering the mirror lens 15 and attaching the lens frame 53 and 56. Further, it is possible to improve strength of the mirror lens 15 using the resin-molded portions 73a and 73b.

The mirror lens 15 has structure in which only the resin-molded portions 73a and 73b are in contact with the mirror lens 15. Therefore, it is possible to further reduce occurrence of peeling of the mirror lens 15 and the lens frames 53 and 56 and further reduce a blur of a visual field due to intrusion of vapor caused by the peeling than structure in which the lens frames 53 and 56 are directly attached to the mirror lens 15.

Figure 14:
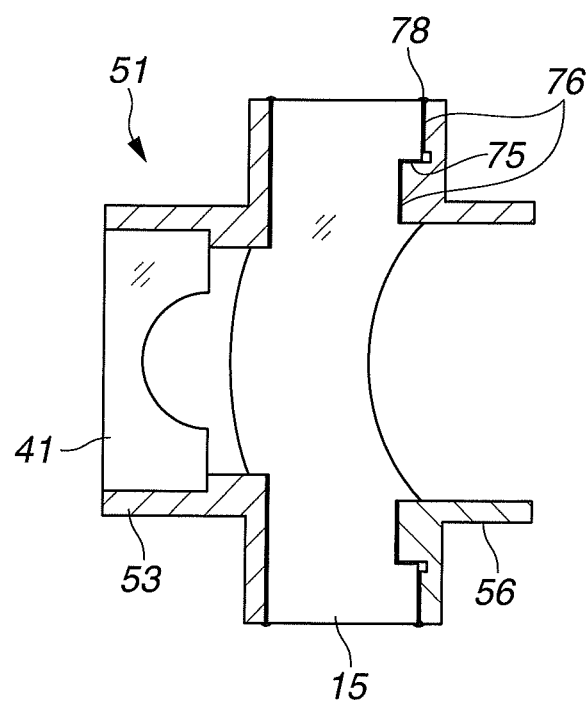
FIG. 14 is an explanatory diagram for explaining structure in which a step portion is provided on a rear surface of the mirror lens to attach the lens frame.

FIG. 14 shows structure in which a step portion is provided in structure of a rear surface side portion of the front lens section 51. On a rear surface of the mirror lens 15 to which a front surface of the lens frame 56 is attached, a step portion 75 dented in a step shape on a small radius side is provided. A rear surface 76 around the step portion 75 is machined in a mirror surface shape to prevent stress from concentrating on the rear surface 76.

In the lens frame 56, a projecting portion 77 convex in a step shape on a small radius side is formed in a front surface portion of the lens frame 56 to correspond to the step portion 75. An outer circumferential surface of the projecting portion 77 is fitted in the step portion 75 to form a fitting surface for centering (alignment). The rear surface of the mirror lens 15 and the front surface of the lens frame 56 to be fit and opposed to each other are fixed by, for example, a hygroscopic adhesive 78.

Note that a front surface side of the mirror lens 15 is not formed in a step shape. The lens frame 53 is fixed to the mirror lens 15 by an adhesive or the like. However, the front surface side of the mirror lens 15 may be formed in step-like structure (step structure). Note that, on an inner side of the lens frame 56, an image pickup section that includes a lens frame to be fitted in the lens frame 56 and to which a rear lens section is attached is arranged.

Such step structure is adopted to form a vapor intrusion preventing trap for effectively preventing vapor from intruding into an optical system on an inner side of the lens frame 53.

Therefore, it is possible to effectively prevent, with the structure shown in FIG. 14, vapor from intruding into the inside of the lens frame 53 and reduce a visual field from being blurred. Note that structure may be adopted for preventing a blue or the like due to intrusion of moisture for a long period by, for example, filling a drying agent such as silica gel or a moisture absorbent or encapsulating drying air in a concavity-like air gap adjacent to the step portion 75.

Embodiments configured by, for example, partially combining the embodiments and the like explained above also belong to the present invention.

What is claimed is:

1. An assembly method for an endoscope image pickup unit including:
   a distal end portion main body portion including a front opening portion, a side opening portion, and a rear opening portion functioning as opening portions respectively opened to a front, a side, and a rear and an arrangement space portion that communicates with the three opening portions;
   a lens section including a distal end lens having an outer diameter that generally fits in the front opening portion; and
   an image pickup section that fits in the rear opening portion and includes an image pickup device arranged in an image forming position by the lens section or an image pickup device arranged in an image forming position by the lens section and a rear lens section arranged to be integrated with the image pickup device in a rear of the lens section,
   the assembly method comprising:
   an inserting step for inserting the lens section into the arrangement space portion from the side opening portion;
   a fitting step for fitting the lens section, which is inserted into the arrangement space portion, in the front opening portion that communicates with the arrangement space portion; and
   an image pickup section fitting step for fitting the image pickup section in the rear opening portion from a rear of the rear opening portion.

2. The assembly method for the endoscope image pickup unit according to claim 1, wherein
   the side opening portion is opened having an area equal to or larger than an area of projection to a side of the lens section to enable the lens section to be inserted from the side and opened having an area smaller than an area of projection to the side of the lens section and the image pickup section after assembly, and
   the rear opening portion is opened having an inner diameter smaller than a maximum outer diameter of the lens section and substantially the same as an outer diameter of the image pickup section.

3. The assembly method for the endoscope image pickup unit according to claim 2, wherein the lens section includes an objective lens for front view for forming an image of an object on a front side of the front opening portion on an image pickup surface as a front-view object image and an objective lens for side view including a reflection surface for, in order to form an image of the object on a lateral side orthogonal to an optical axis direction of the objective lens for front view on the image pickup surface of the image pickup device as a side-view object image, reflecting the image twice, and the assembly method includes, at least after the fitting step, an illumination member arranging step for inserting, from the side opening portion, a side-view illumination member that illuminates a side-view visual field of the objective lens for side view and arranging the side-view illumination member in the side opening portion.

4. The assembly method for the endoscope image pickup unit according to claim 3, wherein the assembly method further includes, after the image pickup section fitting step, a step for performing focusing to form the front-view object image and the side-view object image in a focus state on the image pickup surface of the image pickup device.

5. The assembly method for the endoscope image pickup unit according to claim 4, wherein, in the focusing step, the focusing is performed to respectively form, on the image pickup surface, the front-view object image in a circular region in the focus state and the side-view object image in a substantially annular region on an outer side of the circular region in the focus state.

6. The assembly method for the endoscope image pickup unit according to claim 5, wherein the endoscope image pickup unit mounted on an endoscope is assembled by the assembly method for the endoscope image pickup unit.

7. The assembly method for the endoscope image pickup unit according to claim 3, wherein the endoscope image pickup unit mounted on an endoscope is assembled by the assembly method for the endoscope image pickup unit.

8. The assembly method for the endoscope image pickup unit according to claim 1, wherein the endoscope image pickup unit mounted on an endoscope is assembled by the assembly method for the endoscope image pickup unit.

9. An endoscope comprising;
an image pickup unit including:
a distal end portion main body portion including a front opening portion, a side opening portion, and a rear opening portion functioning as opening portions respectively opened to a front, a side, and a rear and an arrangement space portion that communicates with the three opening portions;
a lens section including a distal end lens having an outer diameter that generally fits in the front opening portion; and
an image pickup section that fits in the rear opening portion and includes an image pickup device arranged in an image forming position by the lens section or an image pickup device arranged in an image forming position by the lens section and a rear lens section arranged to be integrated with the image pickup device in a rear of the lens section, wherein the side opening portion is opened having an area equal to or larger than an area of projection to a side of the lens section to enable the lens section to be inserted from the side and opened having an area smaller than an area of projection to the side of the lens section and the image pickup section after assembly, and the rear opening portion is opened having an inner diameter smaller than a maximum outer diameter of the lens section and substantially the same as an outer diameter of the image pickup section.

10. The endoscope according to claim 9, wherein
the lens section includes an objective lens for front view for forming an image of an object on a front side of the front opening portion on an image pickup surface of the image pickup device as a front-view object image and an objective lens for side view including a reflection surface for, in order to form an image of the object on a lateral side orthogonal to an optical axis direction of the objective lens for front view on the image pickup surface of the image pickup device as a side-view object image, reflecting the image twice, and a side-view illumination member that illuminates a side-view visual field of the objective lens for side view is further arranged adjacent to the lens section in the side opening portion.

11. The endoscope according to claim 10, wherein the image pickup unit is configured to form the front-view object image, which is generated using the objective lens for direct view, in a circular region on the image pickup surface of the image pickup device and form the side-view object image, which is formed using the objective lens for side view, in a substantially annular region on an outer side of the circular region on the image pickup surface of the image pickup device.

12. The endoscope according to claim 11, wherein the image pickup unit includes a first focus adjusting portion for forming the front-view object image in a focus state and a second focus adjusting portion for forming the side-view object image in the focus state.

13. The endoscope according to claim 9, wherein the image pickup unit includes a first focus adjusting portion for forming the front-view object image in a focus state and a second focus adjusting portion for further forming the side-view object image in the focus state before a first adjustment or after the first adjustment.

* * * * *